(12) United States Patent
Tisi et al.

(10) Patent No.: US 7,371,545 B2
(45) Date of Patent: May 13, 2008

(54) METHOD FOR DETERMINING THE AMOUNT OF TEMPLATE NUCLEIC ACID PRESENT IN A SAMPLE

(75) Inventors: Laurence C. Tisi, Ely (GB); James A. H. Murray, Cambridge (GB)

(73) Assignee: Lumora Limited, Cambridge (GB)

( * ) Notice: Subject to any disclaimer, the term of this patent is extended or adjusted under 35 U.S.C. 154(b) by 0 days.

(21) Appl. No.: 10/541,364

(22) PCT Filed: Jan. 14, 2004

(86) PCT No.: PCT/GB2004/000127

§ 371 (c)(1),
(2), (4) Date: Oct. 6, 2005

(87) PCT Pub. No.: WO2004/062338

PCT Pub. Date: Jul. 29, 2004

(65) Prior Publication Data

US 2006/0257874 A1    Nov. 16, 2006

(30) Foreign Application Priority Data

Jan. 14, 2003    (GB) ................................ 0300802.6

(51) Int. Cl.
*C12P 19/34* (2006.01)
(52) U.S. Cl. .................................................. 435/91.2
(58) Field of Classification Search ...................... None
See application file for complete search history.

(56) References Cited

U.S. PATENT DOCUMENTS

| 6,258,568 B1 | 7/2001 | Nyren | |
| 2003/0104372 A1 | 6/2003 | Ahmadian et al. | |
| 2003/0157499 A1 | 8/2003 | Lundeberg et al. | |
| 2003/0165861 A1* | 9/2003 | Wakabayashi et al. | 435/6 |
| 2004/0142330 A1* | 7/2004 | Nyren et al. | 435/6 |
| 2004/0175709 A1 | 9/2004 | Squirrell et al. | |
| 2004/0185457 A1* | 9/2004 | Murray et al. | 435/6 |
| 2004/0197793 A1* | 10/2004 | Hassibi et al. | 435/6 |
| 2006/0257874 A1 | 11/2006 | Tisi et al. | |

FOREIGN PATENT DOCUMENTS

| EP | 0872562 A1 | 10/1998 |
| EP | 0872562 B1 | 9/2002 |
| WO | 98/55653 | 12/1998 |
| WO | 01/42496 A2 | 6/2001 |
| WO | 01/42496 A3 | 6/2001 |
| WO | 02/064830 A2 | 8/2002 |
| WO | 02/090586 A2 | 11/2002 |
| WO | 02/064830 A3 | 5/2003 |
| WO | 03/087388 A2 | 10/2003 |
| WO | WO 2003/087388 A2 | 10/2003 |
| WO | 02/090586 A3 | 11/2003 |
| WO | 203/087388 A3 | 3/2004 |
| WO | 2003/087388 A3 | 4/2004 |
| WO | WO 2003/087388 A3 | 5/2004 |
| WO | WO 2004/062338 A3 | 7/2004 |
| WO | 2004/090167 A1 | 10/2004 |
| WO | WO 2004/090167 A1 | 10/2004 |
| WO | 2004/062338 A3 | 9/2005 |

OTHER PUBLICATIONS

Nyren et al., "Detection of Single-Base Changes Using a Bioluminometric Primer Extension Assay," Analytical Biochemistry, 1997, vol. 244, No. 2, pp. 367-373.*
Nygren et al., "Quantification of HIV-1 Using Multiple Quantitative Polymerase Chain Reaction Standards and Bioluminometric Detection," Analytical Biochemistry, 2001, vol. 288, pp. 28-38.*
Higuchi et al. "Kinetic PCR analysis: Real-time monitoring of DNA amplification reactions" Bio/Technology 11:1026-1030 (1993).
Mori et al. "Detection of loop-mediated isothermal amplification reaction by turbidity derived from magnesium pyrophosphate formation" Biochem. Biophys. Res. Comm. 289:150-154 (2001).
Tabary et al. "Homogeneous phase pyrophosphate (PPi) measurement (H3PIM): A non-radioactive, quantitative detection system for nucleic acid specific hybridization methodologies including gene amplification" J. Immunol. Meth. 156:55-60 (1992).
White et al. "Improved thermostability of the North American firefly luciferase: Saturation mutagenesis at position 354" Biochem. J. 319:343-350 (1996).
definition of "amplification" from *Chambers Science and Technology Dictionary* (Walker ed.), Chambers, p. 31 (1991).
definition of "amplification" from *Medical Ditionary* of MedicineNet.com (http://www.medterms.com) (2001).
Hennard, Int'l Search Report for PCT/GB2004/000127, 4 pages (Jul. 2004).
Hennard, Int'l Preliminary Report on Patentability for PCT/GB2004/000127, 10 pages (Jul. 2005).

\* cited by examiner

*Primary Examiner*—Kenneth R. Horlick
*Assistant Examiner*—Molly Baughman
(74) *Attorney, Agent, or Firm*—Nixon & Vanderhye P.C.

(57) ABSTRACT

A method for determining the amount of template nucleic acid present in a sample comprising the steps of: I) bringing into association with the sample all the components necessary for nucleic acid amplification, and all the components necessary for a bioluminescence assay for nucleic acid amplification and subsequently: ii) performing the nucleic acid amplification, iii) monitoring the intensity of light output from the bioluminescence assay; and iv) determining the amount of template nucleic acid present in the sample.

33 Claims, 12 Drawing Sheets

Figure 1: Set-up used to follow the LAMP reaction
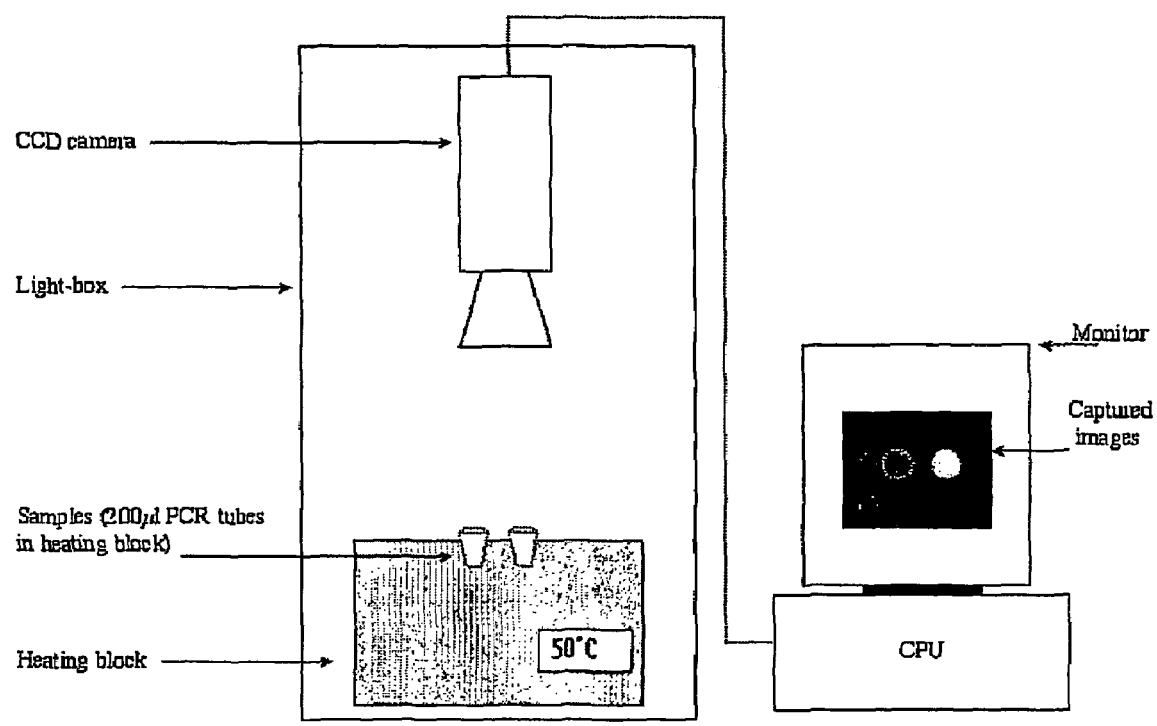

Figure 2: Output from LAMP in the presence of target DNA and in a control without Bst DNA Polymerase
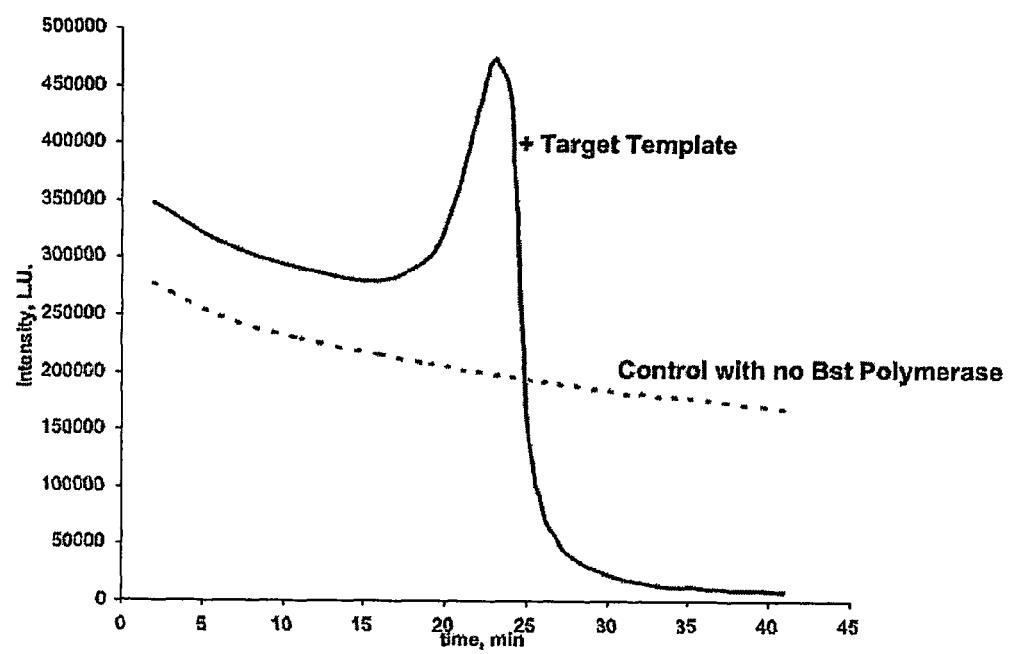

Figure 3: Duplicate LAMP samples and duplicate controls
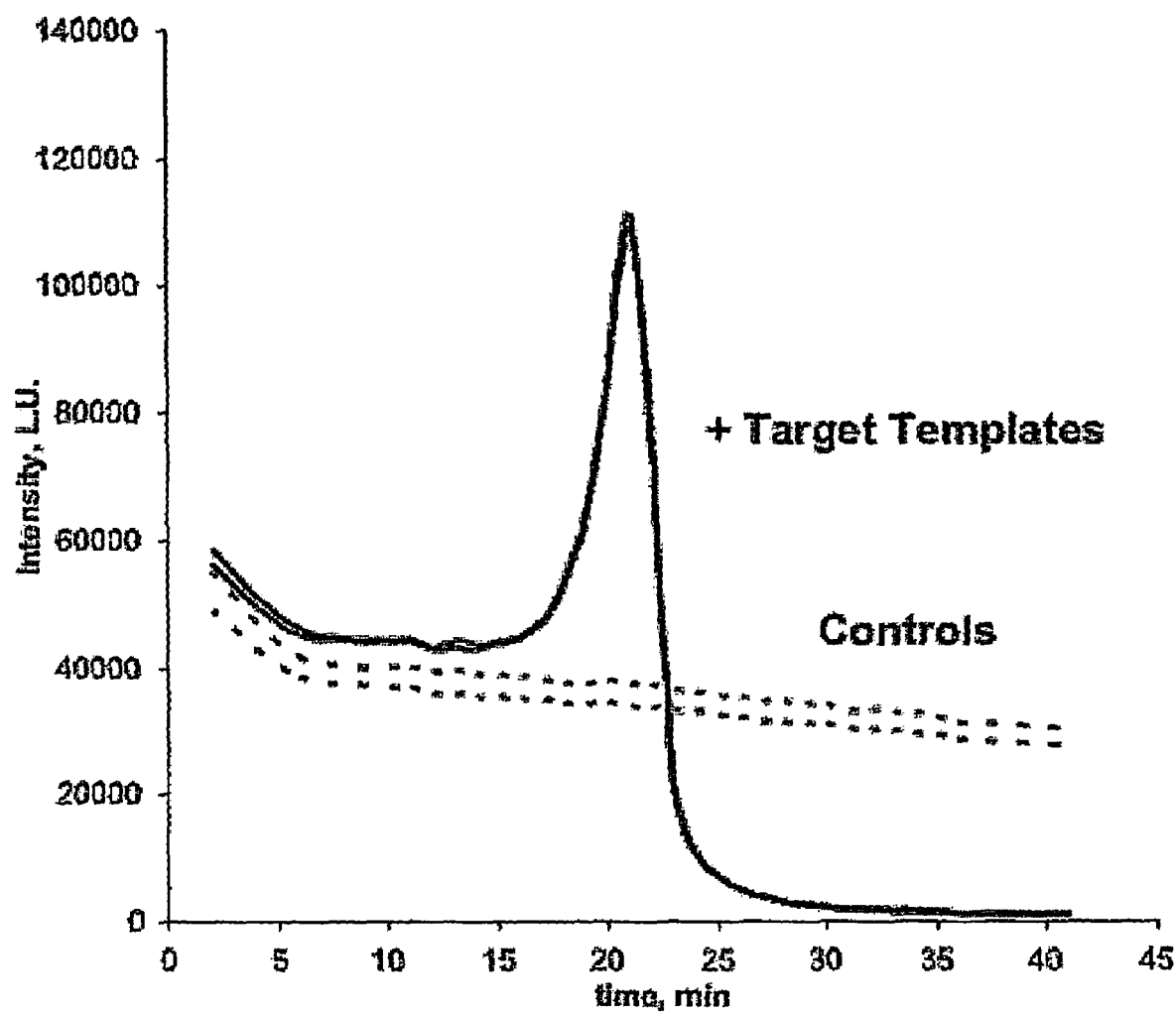

Figure 4: Samples prepared as in Figure 2 & 3 but showing differences in absolute light intensity
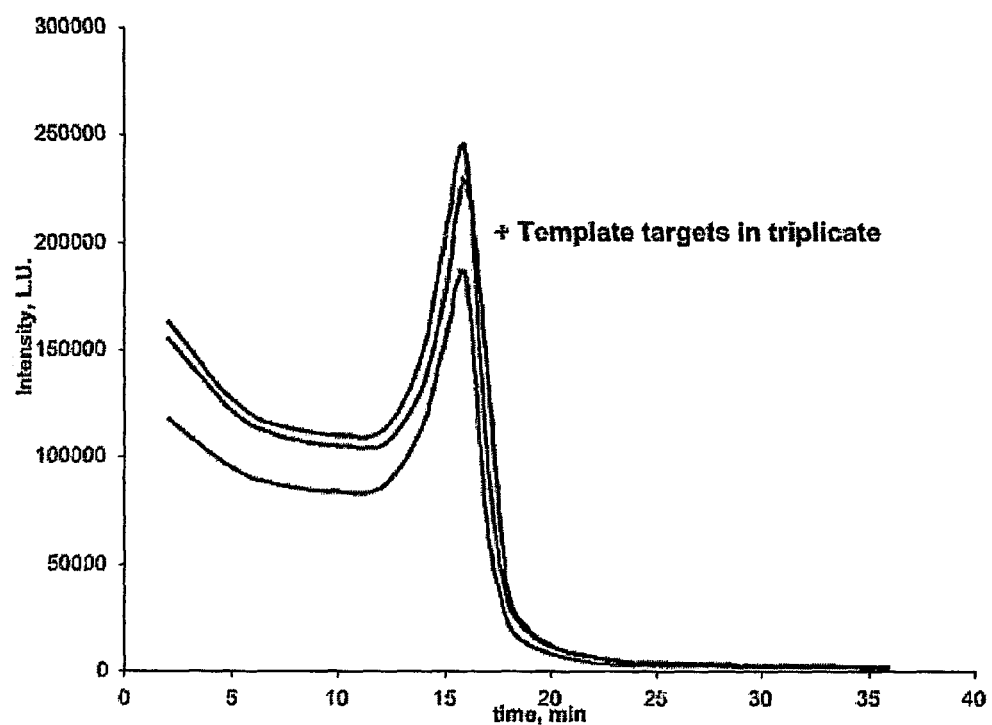

Figure 5: Light emission profiles for LAMP using different amounts of target template (duplicates) at 55°C
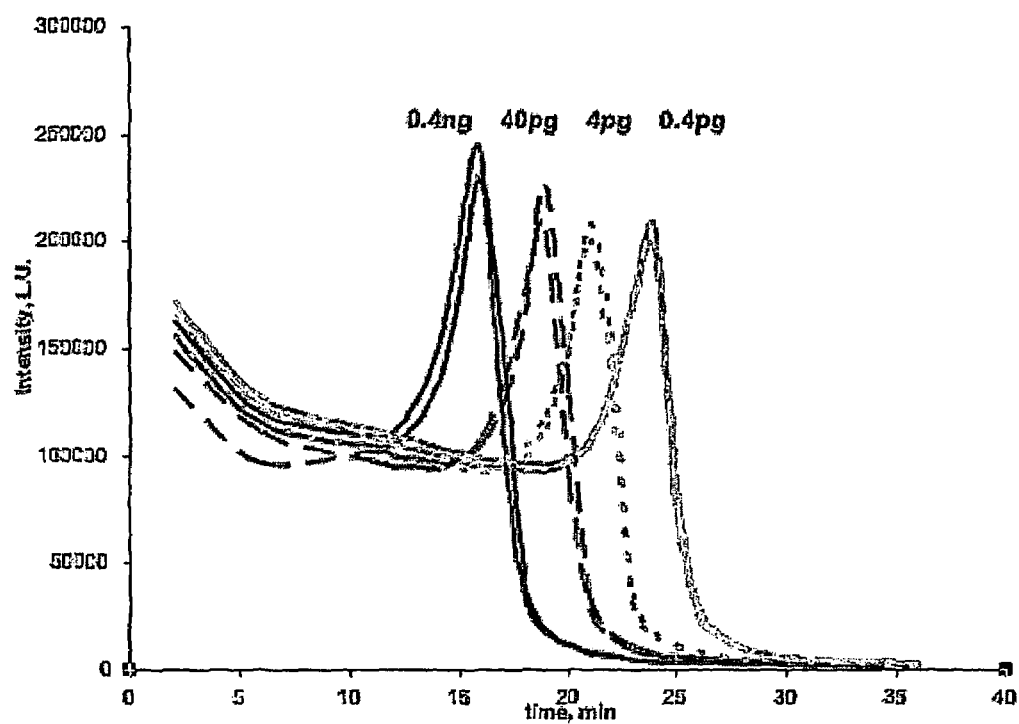

Figure 6: Time to peak light emission
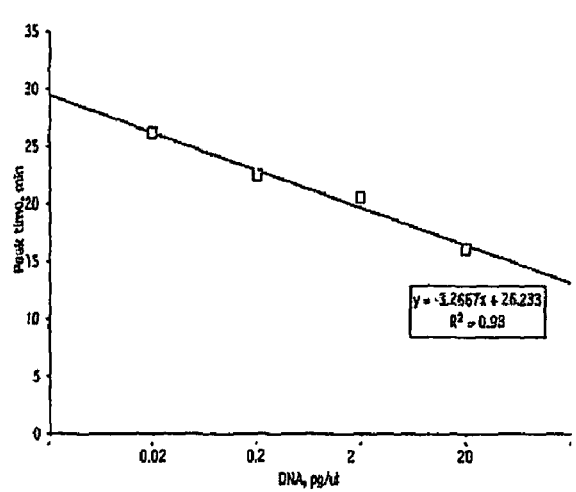
a)
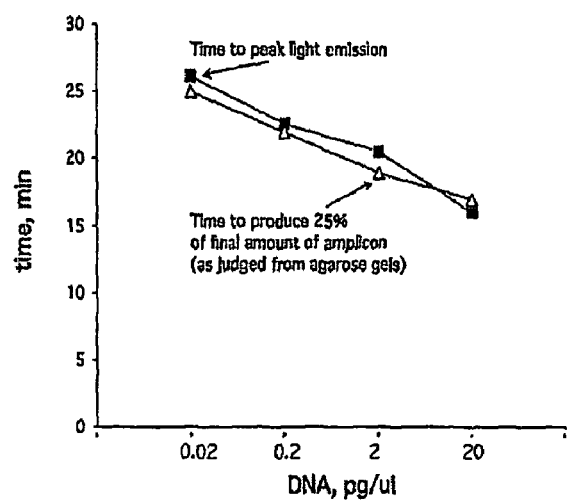
b)

Figure 7: Plot of the raw output from a LAMP reaction in triplicate
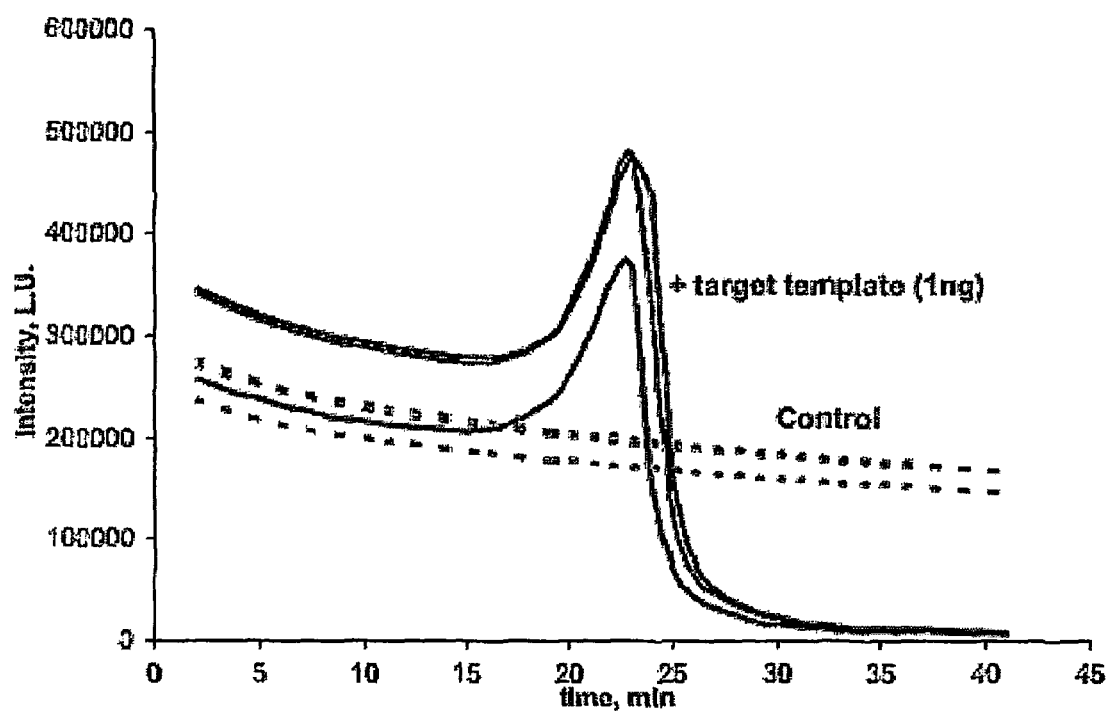

Figure 8: Plots of the 1st derivative of the curves shown in Figure 7
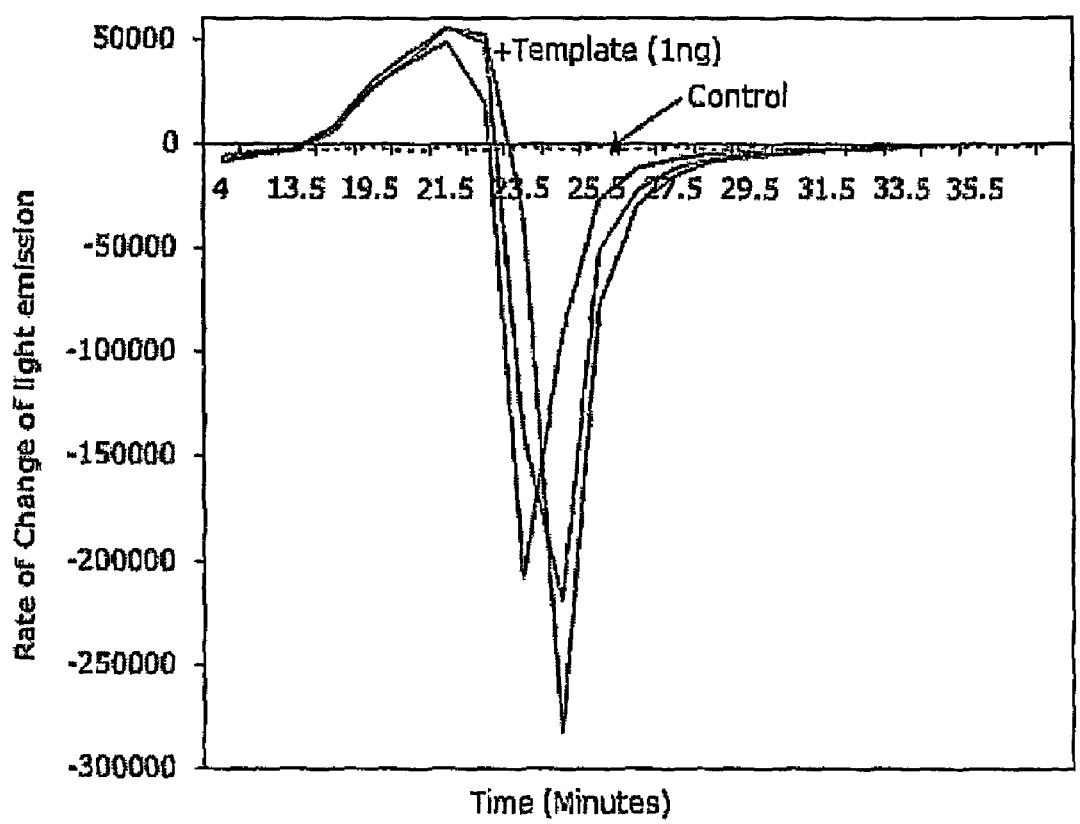

Figure 9: Comparison of controls to samples
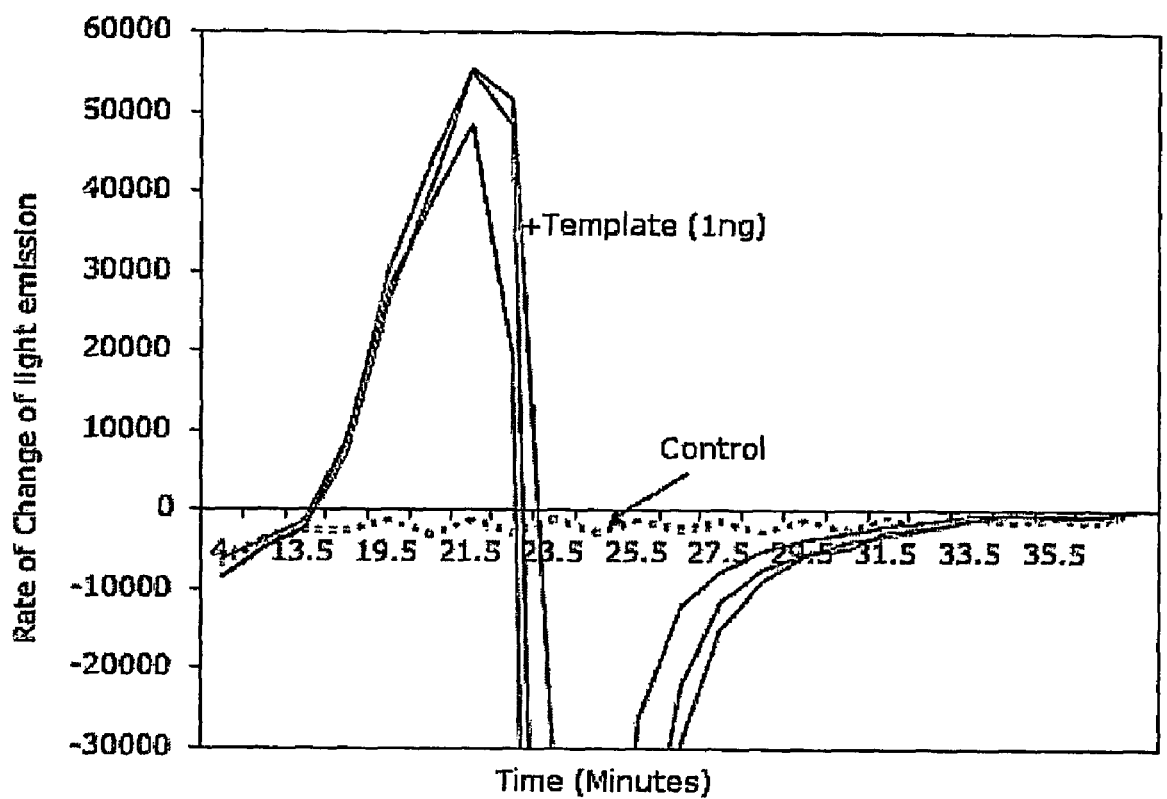

Figure 10: A LAMP reaction where the temperature is decreased from 55°C to 50°C after 10 minutes
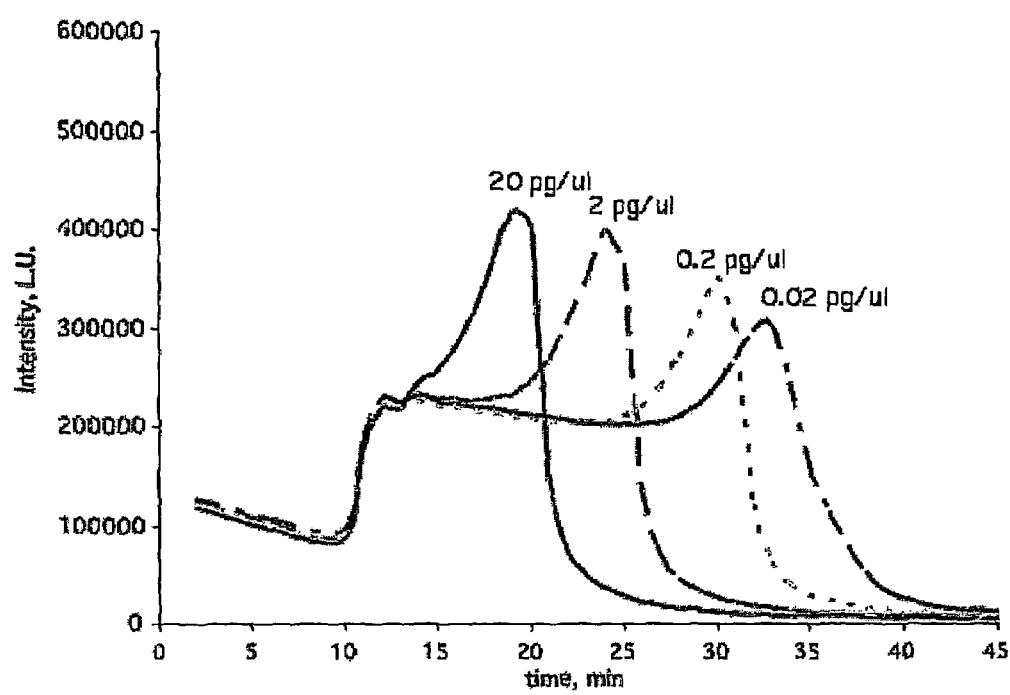

Figure 11: Plot of the light intensity against time for ATP Sulphurylase-free LAMP, with different amounts of starting template
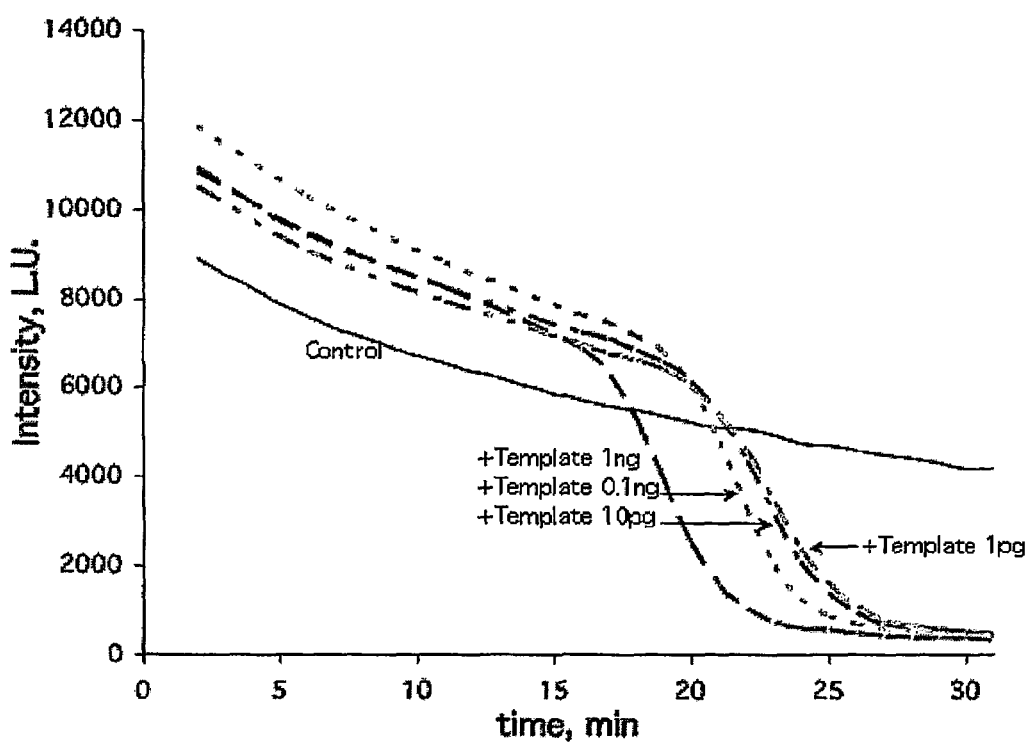

Figure 12: Differential plot (control subtracted) of the normalized light-outputs for the ATP Sulphurylase-free LAMP reactions of samples containing different amounts of target template
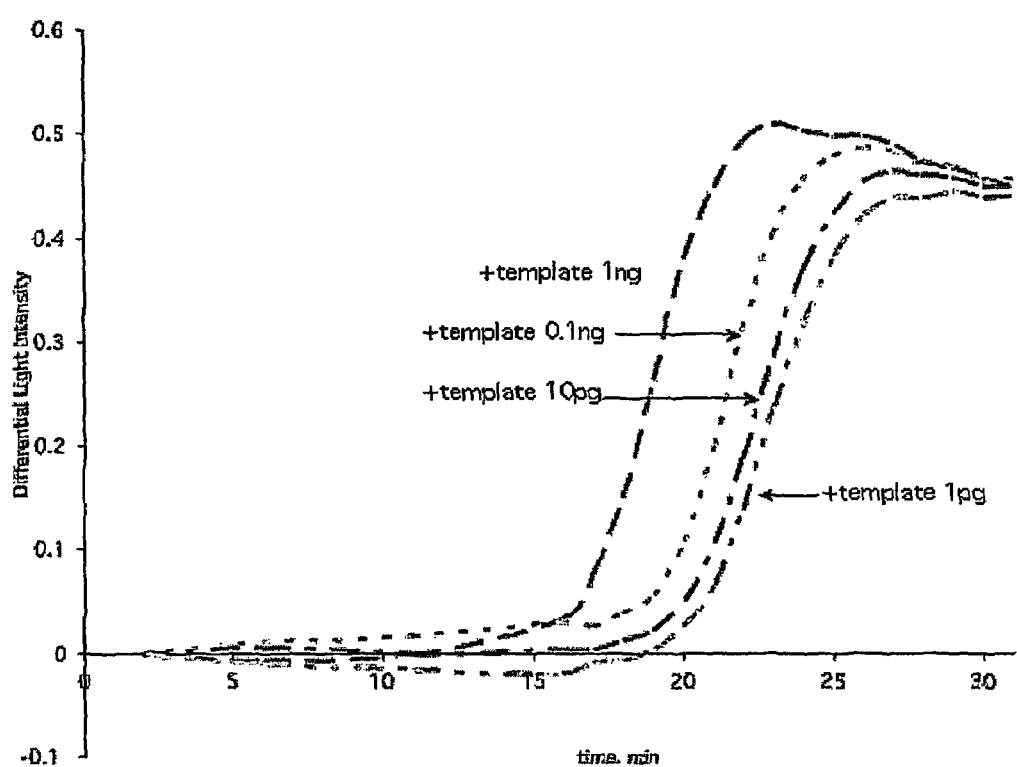

METHOD FOR DETERMINING THE AMOUNT OF TEMPLATE NUCLEIC ACID PRESENT IN A SAMPLE

This application is the U.S. national phase of International Patent Appln. No. PCT/GB2004/000127, filed 14 Jan. 2004, which designated the U.S. and claims priority benefit of GB 0300802.6, filed Jan. 14, 2003; the entire contents of each of which are hereby incorporated by reference.

The invention relates to a method for determining the amount of template nucleic acid present in a sample comprising the steps of: i) bringing into association with the sample all the components necessary for nucleic acid amplification, and all the components necessary for a bioluminescence assay for nucleic acid amplification and subsequently: ii) performing the nucleic acid amplification reaction; iii) monitoring the intensity of light output from the bioluminescence assay; and iv) determining the amount of template nucleic acid present in the sample.

BACKGROUND

Nucleic acid amplification may be used to determine whether a particular template nucleic acid is present in a sample. If an amplification product is produced, this indicates that the template nucleic acid was present in the sample. Conversely, the absence of any amplification product indicates the absence of template nucleic acid in the sample. Such techniques are of great importance in diagnostic applications, for example, for determining whether a pathogen is present in a sample.

Nucleic acids may be amplified by a variety of thermocycling and isothermal techniques. Thermocycling techniques, such as the polymerase chain reaction (PCR), use temperature cycling to drive repeated cycles of DNA synthesis leading to large amounts of new DNA being synthesised in proportion to the original amount of template DNA. Recently, a number of isothermal techniques have also been developed that do not rely on thermocycling to drive the amplification reaction. Isothermal techniques which utilise DNA polymerases with strand-displacement activity have been developed for amplification reactions that do not involve an RNA-synthesis step. Similarly, for amplification reactions that do involve an RNA-synthesis step, isothermal techniques have been developed that use reverse transcriptase, RNase H and a DNA-dependent RNA polymerase.

The products of nucleic acid amplification reactions have traditionally been analysed using gel electrophoresis (either agarose or acrylamide-based) using a fluorescent dye (such as ethidium bromide) to stain for the presence of DNA. This method can be used to indicate the number, amount and size of the amplified products. However, the preparation, running and analysis of amplification reactions using gel electrophoresis requires extensive manual intervention and hazardous reagents and is time-consuming (typically taking around 1 hour in total). In addition, multiple PCR cycles (typically 30) are required to produce detectable product. More recently, methods with increased sensitivity over gel electrophoresis have been developed which rely on fluorescence-based techniques or a turbidity assay to monitor the products of nucleic acid amplification reactions in real-time.

A characteristic of DNA and RNA polymerases is the fact that they release the compound pyrophosphate (PPi) each time they incorporate a new base into the growing DNA/RNA molecule. Thus PPi is produced as a side product in a stoichiometric amount as nucleotides are added to a growing nucleotide chain by the polymerase. Thus it follows that the concentration of PPi is proportional to the amount of nucleic acid synthesis that has occurred and therefore to the accumulation of amplicon. For a polymer of length n, the reaction may be shown as:

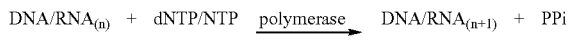

A sensitive assay for PPi is known as the Enzymatic Luminometric Inorganic Pyrophosphate Detection Assay (ELIDA) (see Nyren, P. and Lundin, A., Anal. Biochem. 151: (2) 504-509 (1985)). This assay has two steps: (1) conversion of pyrophosphate (PPi) to ATP by the enzyme ATP sulphurylase, and (2) utilisation of the ATP to produce light in the presence of luciferin and oxygen, catalysed by luciferase:

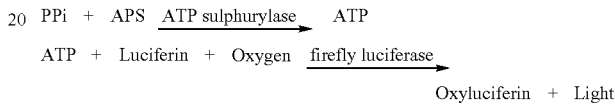

The use of ELIDA-type assays is advantageous in that bioluminescence readings can be rapidly obtained from small sample volumes and the readings can be made using simple, cheap monitoring devices such as photographic film or charge-coupled device (CCD) cameras.

U.S. Pat. No. 5,534,424, U.S. Pat. No. 5,498,523, WO 98/28440, WO 98/13523 and WO 02/20836 describe the use of ELIDA-based methods for sequencing short regions of DNA. The ELIDA assay was used to follow the incorporation of single nucleotides into a DNA molecule by a polymerase during a single round of polymerisation during pyrosequencing. Pyrosequencing is an iterative technique whereby only one of the four deoxynucleotide triphosphates ("dNTPs") is present in each of the iterative assays to enable each deoxynucleotide triphosphate ("dNTP") to be tested at each position of the sequence. Thus all of the components necessary for DNA synthesis are never present simultaneously.

The use of an end-point ELIDA-type assay termed 'H3PIM' for monitoring a thermocycling polymerase chain reaction ("PCR") has also been described (see WO 92/16654 and Tarbary et al., J. Immunological Methods, 156 (1992) 55-60). Aliquots of the reaction mixture were taken at predetermined regular time intervals throughout the reaction process and/or at the end of the amplification process. Thus a lengthy stepwise assay involving the multiple addition of reagents is described.

WO 02/064830 describes the use of an ELIDA assay to perform an end-point assay for monitoring a thermocycling PCR reaction. In WO 02/064830 the ELIDA assay can be performed in a single step, whereas in WO 92/16654 multiple additions and an incubation step are required for monitoring thermocycling PCR as an end-point assay.

There are a number of problems associated with the end-point assays described above. Firstly, they require the components of the bioluminescence assay to be added to the reaction mixture following the amplification reaction. Opening of the tube may lead to contamination of the sample and moreover, to contamination of the laboratory. If the sample itself becomes contaminated then this could result in false-positives or false-negatives being generated. Moreover, if the laboratory becomes contaminated with the amplified template nucleic acid, this increases the likelihood that future samples will become contaminated and false-positive results or false-negative results being obtained (for example, see Victor, T. et al., 'Laboratory experience and guidelines for avoiding false-positive polymerase chain-reactions results', Eur. J. Clin. Chem. & Clin. Biochem., 31(8): 531-535 (1993)). Thus the possibility of contamination represents a severe disadvantage in the use of end-point analysis of this type in diagnostic methods.

A further problem with the use of end-point analysis as described above is that dATP also acts as a substrate for luciferase. Thus when dATP is used as a substrate for the polymerase, spectral interference results from dATP instead of ATP reacting with the luciferase. WO 02/064830 describes how when dATP is used as the substrate in the amplification reaction, the light signal from the ELIDA rapidly decays. This decay would be a serious obstacle to the utility of an endpoint assay as the light reading measured would not only be a function of PPi concentration but also of time. Hence, if the endpoint assays are not performed with strict timing, they will not be quantitative.

An alternative to end-point assays are assays which are able to monitor the synthesis of nucleic acid during an amplification reaction in 'real-time', i.e., as the nucleic acid synthesis is progressing. Existing real-time assays include fluorescence-based techniques and turbidity assays.

Fluorescence-based techniques work by monitoring the change in fluorescence that is associated with the accumulation of an amplification product by some means. For example, methods for monitoring the amplification of DNA during PCR using double-stranded DNA-binding dyes (specifically hybridisation probes containing donor and acceptor fluorophores) are described in U.S. Pat. No. 5,994,056, WO 97/44486, WO 99/42611 and U.S. Pat. No. 6,174,670. These real-time fluorescence-based techniques make it possible to follow PCR without liquid sampling, thus avoiding the need for the reaction tube to be opened and therefore decreasing the risks of contamination.

However, fluorescence-based techniques have significant drawbacks. In particular, the cost of fluorescent reagents, particularly fluorescently-labelled primers, is high and sample preparation can be cumbersome. Further, the application of fluorescence-based systems may be hampered by the limited capacity of equipment and its high cost. Normally, a computer-driven integrated thermocycler-fluorimeter is required as the methods often follow PCR in real-time rather than being employed for end-point analyses. As a result, the accessibility (cost), and portability of such systems is compromised. Since detection is carried out within the PCR instrument, such methods are only available to suitably equipped laboratories.

Real-time turbidity assays involve monitoring the presence or absence of a white precipitate of magnesium pyrophosphate in the amplification reaction mixture as a method of determining whether PPi has been produced. This has been described as a method for determining whether or not an isothermal loop-mediated amplification reaction has occurred (see Mori, Y. et al., 'Detection of loop-mediated isothermal amplification reaction by turbidity derived from magnesium pyrophosphate formation', Biochem. and Biophys. Res. Comm., 289, 150-154 (2001)). However, this method is not very sensitive and requires PPi concentrations of around 0.6 mM before significant turbidity is observed.

SUMMARY OF THE INVENTION

The invention provides a method for determining the amount of template nucleic acid present in a sample comprising the steps of:
i) bringing into association with the sample all the components necessary for nucleic acid amplification, and all the components necessary for a bioluminescence assay for nucleic acid amplification including:
  a) a nucleic acid polymerase,
  b) the substrates for the nucleic acid polymerase,
  c) at least two primers,
  d) a thermostable luciferase,
  e) luciferin,
  f) optionally ATP sulphurylase, and
  g) optionally adenosine 5' phosphosulphate, and subsequently:
ii) performing the nucleic acid amplification reaction;
iii) monitoring the intensity of light output from the bioluminescence assay, and
iv) determining the amount of template nucleic acid present in the sample.

PPi is produced as a consequence of nucleic acid polymerisation during the amplification reaction. A method of the invention involves coupling this production of PPi to light output from the bioluminescence assay. Preferably, the PPi is first converted to ATP. The ATP is then detected by a bioluminescence assay catalysed by a luciferase that uses ATP as a substrate for the production of light in the presence of luciferin and oxygen. Thus the luciferase is used to follow changes in the concentration of ATP. Preferably, this is achieved using an ELIDA-type assay in which PPi is converted to ATP by ATP sulphurylase and then the ATP is used by the luciferase to produce light. Alternatively, PPi is detected directly by the luciferase. By monitoring the intensity of light output from the bioluminescence assay, it is possible to determine how much PPi is present in the reaction mixture and thereby determine the amount of template nucleic acid present in the sample. Thus the method assays the in vitro enzymatic synthesis of nucleic acid and makes it possible to quantify the extent to which the nucleic acid has been amplified as a result of de novo polymerisation during the amplification reaction.

The nucleic acid amplification reaction of step ii) can be equated with a "processive" nucleic acid polymerase reaction in that more than one nucleotide addition cycle is carried out without further additions to or manipulation of the buffer components.

The presence of the luciferase and other components of the bioluminescence assay during the amplification reaction of step ii) greatly simplifies the analysis of the sample as it obviates the requirement for further manipulation of the reaction mixture once the amplification reaction has begun. For example, it is not necessary to take aliquots of the sample in order to determine how much PPi has been produced. Instead, the bioluminescence assay is performed directly on the reaction mixture used for the enzymatic nucleic acid amplification reaction in the presence of all the components necessary for the nucleic acid amplification reaction, i.e., on the reaction mixture that is formed in step i). Neither is it necessary to add the components of the bioluminescence assay to the reaction mixture during or following the amplification reaction.

The components of the bioluminescence assay (also known as the 'pyrophosphate assay' or 'PPi assay') and the amplification reaction must be able to withstand the conditions of the nucleic acid amplification reaction of step ii). For example, a thermostable ATP sulphurylase and/or thermostable luciferase and/or thermostable nucleic acid polymerase can be used. The term 'thermostable' as used herein in relation to an enzyme, refers to an enzyme that is stable within the temperature range at which the nucleic acid amplification reaction of step ii) is carried out.

The components of step i) are preferably stabilised by lyophilisation or by the presence of stabilising factors. Thus stabilisers are also preferably brought into association with the sample in step i). For example one or more of BSA, trehalose, polyvinylpyrrolidone and dithiothreitol (DTT) may be brought into association with the sample in step i). Preferably, all of these stabilisers are brought into association with the sample in step i).

The temperature and time required for nucleic acid amplification reactions are considerably different from those required for nucleic acid polymerisation reactions. Nucleic acid amplification reactions require either a high temperature or a long duration (e.g. 15 minutes to 24 hours) or both. In contrast, nucleic acid polymerisation reactions can be rapidly carried out at low temperatures (e.g. 37° C.). Luciferases are known to be unstable. For example, wild-type firefly luciferase rapidly inactivates at 37° C. Luciferases are also known to be easily inhibited, for example by oxyluciferin, the product of its own light reaction. However, it has surprisingly been found that luciferases can remain stable during the nucleic acid amplification reaction of step ii). Furthermore, it has been found that luciferases can remain stable during the entire course of the nucleic acid amplification reaction of step ii). This is surprising due to the long duration required for certain nucleic acid amplification reactions.

The thermostable luciferase that is brought into association with the sample in step i) is a luciferase enzyme that is stable within the temperature range at which the nucleic acid amplification reaction of step ii) is carried out. The particular luciferase used will depend upon the conditions under which the nucleic acid amplification reaction of step ii) is performed. The term 'luciferase' as used herein refers to an enzyme that catalyses a bioluminescent reaction. Luciferases that are suitable for use in the methods of the invention include both wild-type luciferases and mutant or variant luciferases, provided that these are stable within the temperature range at which the nucleic acid reaction of step ii) is carried out. An example of a thermostable luciferase that is suitable for use in a method of the present invention is the Ultra-Glow thermostable luciferase from Promega.

The nucleic acid amplification reaction of step ii) may or may not involve a RNA synthesis step. In methods in which the amplification reaction of step ii) does not involve an RNA synthesis step, the substrates for the polymerase include each of the four dNTPs: dATP, dTTP, dCTP and dGTP. One or more of the dNTPs may be replaced with a suitable analogue thereof. In these embodiments, the luciferase preferably uses ATP as a substrate for the production of light. Examples of luciferases which use ATP as a substrate for the production of light are firefly luciferase (from *Photinus pyralis*) and mutants thereof. Preferably, the luciferase which uses ATP as a substrate for the production of light is the Ultra-Glow thermostable luciferase from Promega. In embodiments in which the luciferase is used to follow changes in the concentration of ATP, ATP sulphurlyase is present in the reaction mixture. Preferably, the embodiments in which the luciferase is used to follow changes in the concentration of ATP are those embodiments in which the amplification reaction of step ii) does not involve an RNA synthesis step. Alternatively, a luciferase may be used that itself behaves like an ATP sulphurylase in addition to catalysing the bioluminescence assay. In such cases, it is not necessary to add ATP sulphurylase to the reaction mixture in step i).

Adenosine 5' phosphosulphate is required for ATP sulphurylase to produce ATP from PPi and is added to the reaction mixture in step i) when ATP sulphurylase is present and also when a luciferase is used that itself behaves like an ATP sulphurylase in addition to catalysing the bioluminescence assay.

For amplification reactions that do involve an RNA synthesis step, the substrates for the polymerase include each of the four dNTPs (dATP, dTTP, dCTP and dGTP) and each of the four nucleotide triphosphates ("NTPs") (ATP, UTP, CTP and GTP). One or more of the dNTPs and/or NTPs may be substituted by a suitable analogue. Thus when the amplification reaction involves an RNA synthesis step, endogenous ATP is present in the reaction mixture as one of the substrates for the polymerase unless an ATP analogue is used that can be used by the RNA polymerase but does not react with luciferase. Significant amounts of endogenous ATP in the reaction mixture would severely compromise the use of a method of the invention in which the luciferase brought into association with the sample in step i) is required to be sensitive to small changes in the concentration of ATP. In order to overcome this problem, a reversibly-inhibited luciferase is preferably used in embodiments in which the nucleic acid amplification reaction of step ii) involves an RNA-synthesis step and endogenous ATP is present in the reaction mixture. The term 'reversibly-inhibited luciferase' as used herein refers to a luciferase which has become inhibited by a component other than PPi, but which inhibition is relieved by low concentrations of PPi. For example, luciferases are known to become inhibited by oxyluciferin, the product of their own reaction. This inhibition has been found to be relieved by low concentrations of PPi. Thus the use of a reversibly-inhibited luciferase enables PPi to be detected directly by the luciferase since PPi has direct effects on an inhibited luciferase. A series of control reactions using different concentrations of the template nucleic acid can be carried out to determine the time taken for the inhibition of the reversibly-inhibited luciferase to be relieved by PPi for particular concentrations of the template nucleic acid.

The reversibly-inhibited luciferase may be inhibited by a component other than PPi prior to adding the luciferase to the reaction mixture in step i). Alternatively, the reversibly-inhibited luciferase may be formed in situ due to the presence of the inhibitor in the reaction mixture. Preferably, the reversibly-inhibited luciferase is a luciferase that in its uninhibited state uses ATP to produce light. In particular, the luciferase is preferably a beetle luciferase and is preferably a firefly luciferase.

In embodiments in which the luciferase brought into association with the sample in step i) of a method of the invention is a reversibly-inhibited luciferase, ATP sulphurylase and adenosine 5' phosphosulphate are not brought into association with the sample in step i). However, in embodiments in which the nucleic acid amplification reaction of step ii) involves an RNA synthesis step and a suitable ATP analogue that is a substrate for the RNA polymerase but not for luciferase (or at least, is a very poor substrate for luciferase) is brought into association with the sample in step i) rather than ATP itself, then the luciferase that is brought into association with the sample in step i) can be a luciferase which uses ATP for the production of light and then ATP sulphurlyase and preferably adenosine 5' phosphosulphate will then be brought into association with the sample in step i).

A reversibly-inhibited luciferase may also be used in embodiments of the invention in which the nucleic acid amplification reaction of step ii) does not involve an RNA-synthesis step. In such cases, ATP sulphurylase and adenosine 5' phosphosulphate will not be brought into association with the sample in step i).

A further advantage of a method of the invention is the ease with which the light output in step iii) can be detected. Preferably, the intensity of light output in step iii) is monitored visually. Suitable methods for monitoring the intensity of light output include using photographic film or a charge-coupled device (CCD) camera. Alternatively, the intensity monitoring the intensity of light output from the bioluminescence assay using a CCD camera. The light output may be amplified for visualisation where necessary. Thus the ability to detect the light output using only photographic film or a CCD camera has the advantage over techniques which employ fluorescence analysis or gel-based analysis in that no complex hardware or optics are required. Furthermore, the intensity of light output can be monitored without the need to irradiate the sample in any way (as is required in techniques involving fluorescence or absorbance), without the need for any electrochemical interface with the sample (e.g. as in semi-conductor-based approaches: Wilding, P. et al., (1994) 'PCR in a silicon microstructure', Clinical Chemistry, 40(9): 1815-1818) or without the need for indirect irradiation (e.g. as in Surface Plasmon Resonance approaches: Bianchi, N. et al., (1997) 'Biosensor technology and surface plasmon resonance for real-time detection of HIV-1 genomic sequences amplified by polymerase chain reaction', Clinical and Diagnostic Virology, 8(3): 199-208).

Further, one or more than one (for example thousands) of samples, may be monitored simultaneously, for example by a single CCD camera. Thus, a method of the invention may use simple, cheap hardware, with the possibility of portability and miniaturisation and easy integration into high throughput systems.

Step i) of a method of the invention also preferably includes bringing a suitable buffer into association with the sample. Buffers which are suitable for use with a method of the invention include buffers which enable the amplification reaction to proceed and also which enable the bioluminescence assay to proceed. Preferably, the buffer comprises a source of magnesium ions. These are preferably in the form of $MgCl_2$ or $MgSO_4$. For example, a suitable buffer may contain Tris-acetate, potassium chloride, ammonium sulphate, magnesium sulphate and triton X-100 at pH 8.8 at 25° C.

Advantageously, at least steps ii) and iii) of a method according to the invention are carried out in a sealed vessel. This is of great utility since the ability to perform both the amplification reaction and the bioluminescence assay in a sealed vessel reduces or even prevents the possibility of the sample becoming contaminated. Moreover, it reduces or even prevents the possibility of the laboratory becoming contaminated. This is particularly important as if even one copy of the template nucleic acid were to escape into the laboratory, this could potentially contaminate other samples to be tested and give false-positive results. Thus, the ability to prevent contamination is of particular importance where a method of the invention is used in a diagnostic application.

In order to further prevent contamination, following step iv) the vessel is preferably subjected to a suitable treatment in order to destroy the nucleic acid contained in it, in particular to destroy the template nucleic acid. The vessel is itself also preferably destroyed following step iv) or following destruction of the nucleic acid contained in it. This minimises the possibility of the lab and/or further samples becoming contaminated.

Preferably, in step iii) of a method of the invention, the intensity of light output is monitored during the nucleic acid amplification reaction. This is only possible as a result of the components for the bioluminescence assay being present throughout the nucleic acid amplification reaction of step ii). Preferably, the intensity of light output is monitored over the time course of the nucleic acid amplification reaction, i.e., from the beginning to the end of the nucleic acid amplification reaction. Alternatively, the intensity of light output may be monitored during at least a part of the nucleic acid amplification reaction. Alternatively and/or additionally, intensity of light output can be monitored after the nucleic acid amplification reaction of step ii) has finished and/or prior to the amplification reaction of step ii) beginning, for example, in order to take a control reading. The ability to monitor the intensity of light output during the amplification reaction of step ii) simplifies the handling of the reaction vessel and also enables a rapid determination of the amount of template nucleic acid present in the sample. A further advantage of monitoring the intensity of light output during the course of the amplification reaction is that any background signal that is produced by dATP reacting with the luciferase does not interfere with the method of the invention. This only becomes an issue with end-point analysis.

Preferably, step iii) of a method of the invention further includes producing a data set of intensity of light output as a function of time. The data set is used to determine the amount of template nucleic acid present in the sample. Preferably, the data set is analysed by a software application and/or is represented in the form of a graph or a list of figures. For example, the data set may be represented as a plot of light intensity over time or a plot of the rate of change in light intensity over time (i.e., the first derivative).

The intensity of light output may be monitored at one or more predetermined times. These predetermined times are preferably at predetermined times following the time at which all the conditions necessary for the nucleic acid amplification reaction of step ii) to take place are present, at which time (t)=0 mins. Such conditions are that a reaction mixture has been formed as set out in step i) and that the reaction mixture is at a suitable temperature for amplification to proceed, said temperature also being a temperature at which the components of the amplification reaction and the bioluminescence assay are stable. For example, the intensity of light output may be monitored at set predetermined time intervals during at least a part of the amplification reaction. Preferably, the intensity of light output is monitored at set predetermined time intervals during the whole amplification reaction. For example, these intervals could be every 30 seconds, every 1 minute, every 1 minute 30 seconds, etc. Alternatively, the intervals between predetermined times may vary. Preferably, one, two or more light readings are taken per minute. The more readings that are taken per minute, the greater the confidence in the results will be and thus it is preferable to take as many readings per minute as possible. Preferably, the light output is first monitored at time=0 mins. In certain embodiments, the intensity of light output may also be monitored after the amplification reaction has finished.

The greater the sensitivity of the light detection system being used, the more time points per minute are possible since when using a more sensitive camera, each datum comes from integrating the light emission over a shorter time than with a less sensitive CCD camera. Thus it is advantageous to use as sensitive a camera as possible.

Advantageously, in step iii) of a method of the invention, the intensity of light output is monitored continuously. Preferably, the light output is monitored continuously during at least a part of the amplification reaction of step ii). More preferably, the light output is monitored continuously during the whole of the amplification reaction of step ii). Step iii) also encompasses alternatively or additionally monitoring the intensity of the output of light continuously after the amplification reaction of step ii) has finished.

A method according to the invention may be used to determine the amount of template nucleic acid present in a sample in a quantitative fashion and/or in a qualitative fashion.

Use in a quantitative fashion includes the use of a method of the invention to determine the amount of template present in a sample prior to the nucleic acid amplification reaction of step ii) occurring. It also includes the use of a method of the invention to determine the amount of template nucleic acid present in a sample as a result of the amplification reaction of step ii), which may be determined either during or following the nucleic acid amplification reaction of step ii); i.e., the quantification of how much nucleic acid amplification product ("amplicon") has been produced. This makes it possible to quantify the extent of the nucleic acid amplification reaction. When used in a quantitative fashion, the term 'determine' includes both an accurate determination of the amount of template nucleic acid present in the sample and an estimate of the amount of template nucleic acid present in the sample.

It has surprisingly been found that in order to determine the amount of template nucleic acid present in a sample in a quantitative fashion, the timing of the change in intensity of light output is a proportionate factor in addition to the intensity per se of the light output produced. For example, for a particular set of reaction conditions (e.g., a particular template nucleic acid, a particular concentration of components for the amplification reaction and the bioluminescence assay and a particular temperature(s) for the amplification reaction), if a higher concentration of template nucleic acid is present in the sample at the beginning of the nucleic acid amplification reaction, the changes in intensity of light output will occur after a shorter period of time following the start of the amplification reaction when compared to a reaction in which a lower concentration of template nucleic acid is present in the sample. Thus, for a particular set of reaction conditions, it is possible to determine the amount of template nucleic acid that is present in the sample by monitoring the change in intensity of light output as a function of time. Preferably, a series of control reactions are performed using different known concentrations of the particular template nucleic acid under the particular set of reaction conditions and the results obtained from the sample under analysis by a method of the invention are compared to the results obtained from this series of control reactions. A control can also be performed wherein the amount of template nucleic acid that has been produced during the amplification reaction at predetermined time points is assessed using gel electrophoresis or another suitable quantitative method. This will enable the amount of template nucleic acid in the control sample at the predetermined time point to be calculated and correlated with the respective points on the data set.

When used in a qualitative fashion, a method of the invention can be used to assess whether or not a nucleic acid amplification reaction has produced any amplification product and thereby determine whether any template nucleic acid is present in the sample. In many applications where the amplification conditions are already sufficiently optimised (e.g. rapid detection of nucleic acid (preferably DNA) associated with pathogens), the only information required to establish that the target DNA sequence was present in a sample is the occurrence of the amplification reaction. Where template nucleic acid is present in the sample, this will result in amplicon being produced as a result of the nucleic acid amplification reaction of step ii). Consequently, this will result in a change in the pattern of the intensity of light output as a function of time when compared to a control reaction in which no amplification has taken place. Where no template nucleic acid is present in the sample, no amplification reaction will take place in step ii) and thus no amplicon will be produced as a result. Consequently, the pattern of change in intensity of light output as a function of time will be similar if not the same as a control in which no amplification has taken place. Thus, the expression 'performing the nucleic acid amplification reaction' as used in step ii) includes both 'performing the nucleic acid amplification reaction' and also 'creating the appropriate conditions for the amplification reaction to occur', since in embodiments in which there is no template nucleic acid present in the sample, no nucleic acid amplification reaction will occur. Preferably, the presence or absence of the expected light change is monitored with a predetermined period of time following the start of the reaction.

As mentioned above, it has also been found that PPi can itself have direct effects on luciferase at high concentrations. This applies to both luciferases that use ATP as a substrate for the production of light and also reversibly-inhibited luciferases. By carrying out a number of control experiments using different concentrations of a particular starting template nucleic acid under a particular set of reaction conditions, the skilled person will be able to determine from the data set the time at which PPi itself has a direct effect on the luciferase. These control results can then be used to extrapolate the amount of template nucleic acid present in the sample.

For example, it has been found that PPi can itself inhibit luciferase at high concentrations. The point at which the intensity of light output begins to rapidly decrease correlates with the point at which the luciferase has become inhibited by a particular concentration of PPi. This may correspond to the point at which the intensity of light output is at a maximum, i.e., the point which marks the transition between the light output increasing and the light output decreasing. Alternatively, it may represent the point at which the rate of decrease in intensity of light output significantly increases, e.g. from a gradual decrease to a rapid decrease. By carrying out a number of control experiments using different concentrations of template nucleic acid, the time at which the intensity of light output begins to rapidly decrease for each particular starting template nucleic acid concentration under a particular set of reaction conditions can be determined. These control results can then be used to extrapolate the amount of template nucleic acid present in the sample.

Alternatively, PPi may cause an increase in light emission from a luciferase inhibited by a substance other than PPi, as in the reversibly-inhibited luciferase embodiment mentioned above.

Thus whether or not PPi stimulates or inhibits the bioluminescence assay catalysed by luciferase depends on a number of factors including the precise type of luciferase used, the temperature of the reaction, the concentration of PPi and the presence of other compounds that can affect luciferase activity. By carrying out a number of control experiments using different concentrations of a particular starting template nucleic acid under a particular set of reaction conditions, the skilled person will be able to determine from the data set the time at which PPi itself has a direct effect on the luciferase and the nature of this effect. These control results can then be used to extrapolate the amount of template nucleic acid present in the sample.

The data set of intensity of light output as a function of time can be interpreted in a number of different ways in order to determine the amount of template nucleic acid present in the sample. Particular points on the data set represent points in time at which specific concentrations of PPi are present. These can then be correlated to the amount of template nucleic acid present in the sample. For example, one or more of the following points on the data set are preferably monitored: i) the time taken to reach the point at which the intensity of light output begins to increase; ii) the time taken to reach the point at which the rate of change of increase of intensity of light output increases or decreases; iii) the time taken to reach the point at which the rate of change of intensity of light output changes from an increase to a decrease (this is preferably the point of maximum intensity of light output or "peak" intensity of light output) or from a decrease to an increase; iv) the time taken to reach the point at which the rate of change of decrease in intensity of light output increases or decreases, and/or v) the time taken to reach the point at which the intensity of light output reaches or crosses a predetermined level.

For determination of the amount of template nucleic acid present in the sample in a quantitative fashion, the points on the data set which are monitored are preferably those points at which the rate of change in intensity of light output changes significantly. When interpreting the data set, the points at which the rate of change in intensity of light output changes significantly will be apparent to the skilled person.

Most preferably, a point at which the rate of change in intensity of light output changes significantly will be a point which represents a transition between the intensity of light output increasing and the intensity of light output decreasing. A point which represents a transition between the intensity of light output decreasing and the intensity of light output increasing is also a point at which the rate of change in intensity of light output changes significantly. A point which marks a transition between the intensity of light output increasing and decreasing or decreasing and increasing will preferably be represented as an inflection point when the results are displayed on a graph of intensity of light output as a function of time. A point at which the intensity of light output changes from a constant intensity to an increase or decrease in intensity, or a point at which the intensity of light output changes from an increase or decrease in intensity to a constant intensity also represents a point at which the rate of change in intensity of light output changes significantly.

Alternatively, a point at which the intensity of light output changes significantly may be a point at which the rate of increase in intensity of light output or the rate of decrease in intensity of light output significantly increases or decreases. Thus, the expression 'a point at which the rate of change in intensity of light output changes significantly' preferably refers to a point at which the rate of change in intensity of light output at a predetermined time interval before that points differs by at least 30% from the rate of change in intensity of light output at the same predetermined time interval after that point. More preferably, 'a point at which the rate of change in intensity of light output changes significantly' refers to a point at which the rate of change in intensity of light output at a predetermined time interval before that points differs by at least 50% from the rate of change in intensity of light output at the same predetermined time interval after that point. Even more preferably, 'a point at which the rate of change in intensity of light output changes significantly' refers to a point at which the rate of change in intensity of light output at a predetermined time interval before that points differs by at least 70% from the rate of change in intensity of light output at the same predetermined time interval after that point. Alternatively, 'a point at which the rate of change in intensity of light output changes significantly' refers to a point at which the rate of change in intensity of light output at a predetermined time interval before that point differs by at least 10%, 20%, 40%, 60% or 80% from the rate of change in light intensity at the same predetermined time interval after that point. The predetermined time interval is preferably 30 seconds but may alternatively be 1 minute, 1 minute 30 seconds or more. Alternatively, the predetermined time interval may be less than 30 seconds. The chosen predetermined time interval will depend upon the time intervals at which the intensity of light output is monitored and will depend upon the kinetics of the particular amplification reaction that is being studied.

Thus for quantitative determination, one or more of the following points on the data set are preferably monitored: i) the point at which the intensity of light output begins to increase; ii) the point at which the rate of change of increase of intensity of light output significantly increases or decreases; iii) the point at which the rate of change of intensity of light output changes from an increase to a decrease (preferably the point of maximum intensity of light output) or from a decrease to an increase and/or iv) the point at which the rate of change of decrease in intensity of light output significantly increases or decreases. The time at which the intensity of light output reaches or crosses a predetermined level may also be monitored.

In embodiments in which a reversibly-inhibited luciferase is not used, the amount of nucleic acid present in the sample is preferably determined in a quantitative fashion by monitoring one or more of the following points: i) the time taken to reach a point at which the intensity of light output to begin to increase; ii) the time taken to reach a point at which the rate of change of intensity of light output to change from an increase to a decrease; iii) the time taken to reach a point at which the rate of change of decrease in intensity of light output significantly increases; iv) the time taken to reach a point at which the rate of change of decrease in intensity of light output significantly decreases; and v) the time taken for the intensity of light output to reach or cross a predetermined level.

In embodiments in which a reversibly-inhibited luciferase is used, whilst the luciferase is inhibited by the product of its reaction, the intensity of output of light decreases gradually. Then, once a certain amount of PPi is produced as a result of the amplification reaction, the luciferase becomes sensitive to PPi and thus uninhibited and the intensity of light output increases. The intensity of light output then gradually decreases until a certain amount of PPi has been produced at which point, the rate of change of decrease in intensity of light output increases and the intensity of light output then decreases to a level that is less than the intensity of light output of a control reaction in which no nucleic acid amplification has taken place. The rate of change of decrease of intensity of light output then decreases. Thus, in embodiments in which a reversibly-inhibited luciferase is brought into association with the reaction mixture in step i), the amount of template nucleic acid present in the sample is preferably determined in a quantitative fashion by monitoring one or more of the following points: i) the time taken to reach a point at which the intensity of light output changes from a gradual decrease to an increase (i.e. the point at which the intensity of light output begins to increase); ii) the time taken to reach a point at which the rate of decrease in the intensity of light output significantly increases (preferably from a gradual decrease to a rapid decrease); and iii) the time taken to reach a point at which the rate of decrease in the intensity of light output significantly decreases (preferably from a rapid decrease to a gradual decrease).

As mentioned above, the time it takes to reach a particular point for a particular template nucleic acid depends upon the concentration of template nucleic acid present in the sample at the beginning of the amplification reaction. Thus, step iv) of a method of the invention preferably further comprises comparing the intensity of light output to the intensity of light output from a standard curve formed by the results from a number of controls in which the samples comprise known amounts of template nucleic acid in order to determine the amount of template nucleic acid in the sample.

For determination of the amount of template nucleic acid present in the sample in a qualitative fashion, i.e., whether or not the template nucleic acid is present in the sample, the point on the data set which is monitored is preferably the point at which the intensity of light output reaches or crosses a predetermined level.

In embodiments in which a reversibly-inhibited luciferase is not used, an increase in the intensity of light output will indicate the presence of template nucleic acid in the sample. Preferably, the increase in intensity of light output is relative to a control reaction in which no amplification has taken place. For example, such a control reaction will preferably be one in which no template nucleic acid is present or one in which no polymerase is present. Thus, in these embodiments, the amount of nucleic acid present in the sample may be determined in a qualitative fashion by monitoring whether the intensity of light output rises above that of a control in which no amplification has taken place. More preferably, in these embodiments, the amount of nucleic acid present in the sample may be determined in a qualitative fashion by monitoring whether the intensity of light output reaches or rises above a predetermined level. For example, the predetermined level could be set at 125% or 150% of the light output at the beginning of the amplification reaction at the point at which the rate of decrease in light intensity is at a minimum. If the intensity of light output reaches this predetermined level or increases beyond it, this will indicate the presence of template nucleic acid in the sample. However, if the intensity of light output does not reach this predetermined level, this will indicate the absence of template nucleic acid in the sample.

The predetermined level may vary depending on one or more factors including: the template nucleic acid used, the concentration of the components used in the nucleic acid amplification reaction and the temperature used for the nucleic acid amplification reaction. By carrying out control experiments in which template nucleic acid is present or template nucleic acid is not present, the skilled person will readily be able to determine a suitable predetermined level.

Preferably, the presence of the increase in the intensity of light output within a predetermined length of time following the start of the amplification reaction of step ii) indicates the presence of template nucleic acid in the sample and the absence of the increase in the intensity of light output within the predetermined length of time following the start of the amplification reaction of step ii) indicates the absence of template nucleic acid in the sample. For example, where a method of the invention is used for genotyping, where a certain amount of test material would always contain a certain amount of target template, then if the target template nucleic acid is present, one can confidently state that if the intensity of light output has not increased within a predetermined time, then the target is absent.

Preferably, the predetermined length of time will be a time which occurs during the amplification reaction of step ii). The less template nucleic acid that is present at the beginning of the reaction, the longer the amplification reaction of step ii) takes. By carrying out a number of control experiments for a particular template nucleic acid under a particular set of reaction conditions in which template nucleic acid is present at varying concentrations or template nucleic acid is not present, the skilled person will readily be able to determine a suitable predetermined time by which the increase must have or must not have occurred for that particular template nucleic acid under that particular set of reaction conditions. For example, the predetermined length of time may be within 20, 25, 30, 35, 40, 45, 50 or more minutes from the start of the nucleic acid amplification reaction.

Alternatively or additionally, in a method according to the invention, a decrease in the intensity of light output relative to a predetermined level indicates the presence of template nucleic acid in the sample. It is hypothesised that this decrease occurs when the luciferase becomes inhibited by PPi. For example, the predetermined level could be set at 25%, 20%, 15%, 10% or 5% of the light output at the beginning of the amplification reaction at the point at which the rate of decrease in light intensity is at a minimum. If the intensity of light output decreases to this predetermined level or decreases beyond it, this will indicate the presence of template nucleic acid in the sample. However, if the intensity of light output does not reach this predetermined level, this will indicate the absence of template nucleic acid in the sample.

The predetermined level may vary depending on one or more factors including: the template nucleic acid used, the concentration of components used in the nucleic acid amplification reaction and the temperature of the nucleic acid amplification reaction. By carrying out control experiments in which template nucleic acid is present or template nucleic acid is not present, the skilled person will readily be able to determine a suitable predetermined level.

Step iv) of a method of the invention preferably further comprises comparing the intensity of light output to the intensity of light output from a control in which no amplification has taken place. For example, such a control may be one in which the same steps are carried out as in a method according to the invention except that either the template nucleic acid and/or one of the other components needed for the amplification reaction (e.g. the polymerase) is/are omitted. This allows the decay of bioluminescence over time to be taken into account.

In a method according to the invention, although a control is preferably run simultaneously to the sample under analysis, it is not necessary for this to be the case. For example, the control may be a control which has been run previously and the data obtained therefrom could be used for comparison with numerous other samples.

In a method according to the invention, a decrease in the intensity of light output relative to a control reaction in which no amplification has taken place indicates the presence of template nucleic acid in the sample. This decrease relative to the control will occur subsequent to the other changes in intensity of light output relative to the control that are described above. The finding that the intensity of light output eventually decreases to a level that is less than a control reaction in which no amplification has taken place is surprising as the skilled person would expect the intensity of light output to continue to increase as more PPi is produced. It is hypothesised that the intensity of light output decreases to a level less than the control because the luciferase becomes inhibited by PPi. Although the monitoring of the intensity of light output to determine whether it is less than that of a control in which no amplification has taken place is preferably carried out during the amplification reaction of step ii), it may alternatively be carried out following the nucleic acid amplification reaction of step ii). Preferably, the intensity of light output decreases to a level that is 30% or less of the intensity of light output of the control reaction. More preferably, the intensity of light output decreases to a level that is 20% or less of the intensity of light output of the control reaction. Even more preferably, the intensity of light output decreases to a level that is 10% or less of the intensity of light output of the control reaction. Alternatively, the intensity of light output may decrease to a level that is 90% or less, 80% or less, 70% or less, 60% or less, 50% or less or 40% or less of the intensity of light output of the control reaction.

Preferably, the presence of the decrease in the intensity of light output relative to the predetermined level or to the control reaction within a predetermined length of time following the start of the nucleic acid amplification reaction indicates the presence of template nucleic acid in the sample and the absence of the decrease in the intensity of light output relative to the predetermined level or to the control reaction within the predetermined length of time following the start of the amplification reaction indicates the absence of template nucleic acid in the sample. The predetermined length of time is preferably within 20, 25, 30, 35, 40, 45, 50 or more minutes from the start of the nucleic acid amplification reaction. By carrying out control experiments in which different concentrations of template nucleic acid are present or template nucleic acid is not present, the skilled person will readily be able to determine a suitable predetermined time by which the decrease must have or must not have occurred.

The nucleic acid amplification reaction of step ii) is preferably carried out within a temperature range in which the luciferase is sufficiently active and stable to give sufficient and stable light output over the duration of the amplification reaction. Further, the amplification reaction of step ii) is preferably one that can be performed at a low enough temperature and that is rapid enough for the luciferase to remain stable during the amplification reaction. The nucleic acid amplification reaction of step ii) of a method of the invention may be carried out isothermally or may be a thermocycling method. Preferably, the nucleic acid amplification reaction of step ii) of a method of the invention is carried out isothermally. Nucleic acid amplification reactions which are carried out isothermally are those nucleic acid amplification reactions which do not rely on thermocycling for the amplification reaction to proceed.

Examples of nucleic acid amplification reactions which do not involve a RNA synthesis step and which are suitable for monitoring by a method according to the invention include both isothermal methods and also thermocycling methods such as PCR.

Isothermal methods which do not involve an RNA synthesis step proceed via strand displacement. Such methods include: rolling circle amplification (see Fire, A. and Xu, S.-Q. (1995) 'Rolling replication of short DNA circles', Proc. Natl. Acad. Sci. USA, 92, 4641-4645), rolling circle amplification technology (see http://www.molecularstaging-.com/Pages/RCATdetails_.html; Amersham's Phi29-based amplification Kit, product codes: 25-6400-10 and 25-6400-50), isothermal ramification amplification (Zhang, W. et al., 'Detection of *Chlamydia trachomatis* by isothermal ramification amplification method: a feasibility study', J. Clin. Microbiol., January 2002, 128-132), restriction-endonuclease-dependent strand displacement amplification (Walker, G. T., 'Isothermal in vitro amplification of DNA by a restriction enzyme/DNA polymerase system', PNAS, (1992), 89, 392-396), loop-mediated isothermal amplification (LAMP) (Notomi, T., 'Loop-mediated isothermal amplification of DNA', Nucl. Acids. Res., 2000, 28(12), e63, i-vii) and variants of these methods. Isothermal nucleic acid amplification techniques that do not involve an RNA-synthesis step and which proceed via strand-displacement mechanisms are also known as 'isothermal PCR' techniques. The finding that a bioluminescence assay based on an ELIDA assay can be used to monitor amplification reactions that proceed via strand displacement is surprising given the number of background reactions that occur due to the low temperature of the amplification reaction.

Alternatively, thermocycling methods which do not involve an RNA synthesis may be used in a method of the invention provided that all the components of the amplification reaction and the bioluminescence assay are stable at the temperatures through which the PCR cycles. Preferably, the thermocycling reaction is a low temperature thermocycling method in which primer extension is carried out in a cycling temperature range that does not exceed 75° C. and which preferably does not exceed 70° C. and which utilises a moderately thermostable DNA polymerase. Such a method is LoTemp® PCR which uses a HiFi® DNA polymerase and is described at www.hifidna.com/FQAall.htm. Alternatively, the thermocycling reaction is a low temperature thermocycling method which utilises the Klenow fragment of DNA polymerase I in the presence of proline (see Nucleic Acid Research, (1999), 27(6), 1566-1568).

Examples of isothermal amplification reactions that involve an RNA synthesis step and that can be monitored by a method of the invention include transcription mediated amplification (TMA) or nucleic acid sequence based amplification (NASBA) (Guatelli, J. C. et al., 'Isothermal, in vitro amplification of nucleic acids by a multienzyme reaction modelled after retroviral replication', PNAS, (1990), 87, 1874-1878) and variants of these methods.

The nucleic acid amplification reaction of step ii) is carried out within a temperature range within which the components of the amplification reaction and the bioluminescence assay remain stable. Preferably, the nucleic acid amplification reaction of step ii) is carried out within a temperature range that does not exceed 75° C. More preferably, the nucleic acid amplification reaction of step ii) is carried out within a temperature range that does not exceed 70° C. Even more preferably, the nucleic acid amplification reaction of step ii) is carried out within a temperature range that does not exceed 65° C. Most preferably, the nucleic acid amplification reaction of step ii) is carried out within a temperature range that does not exceed 60° C., i.e., a temperature range within which the Ultra-Glow thermostable luciferase from Promega is sufficiently active and stable to give sufficient and stable light output over the duration of the amplification reaction. Alternatively, the nucleic acid amplification reaction of step ii) may be carried out within a temperature range that does not exceed 55° C., 50° C., 45° C. or 40° C.

Preferably, the nucleic acid amplification reaction of step ii) is carried out within a temperature range that does not go below 20° C. More preferably, the nucleic acid amplification reaction of step ii) is carried out within a temperature range that does not go below 30° C. Even more preferably, the nucleic acid amplification reaction of step ii) is carried out within a temperature range that does not go below 40° C. Alternatively, the nucleic acid amplification reaction of step ii) may be carried out within a temperature range that does not go below 25° C., 35° C., 45° C., 50° C., 55° C. or 60° C.

Preferably, the nucleic acid amplification reaction of step ii) is carried out within a temperature range of 30° C. to 75° C. More preferably, the nucleic acid amplification reaction of step ii) is carried out within the temperature range of 30° C. to 65° C. For example, the nucleic acid amplification reaction of step ii) may be carried out within the temperature range of 45° C. to 65° C. or 35° C. to 40° C.

The nucleic acid amplification reaction of step ii) may be carried out at a constant temperature within the temperature ranges specified above. In a preferred embodiment, the nucleic acid amplification reaction is carried out at 37° C. For example, by using a mutant firefly luciferase enzyme that is stable at 37° C. (wild-type enzyme rapidly inactivates at this temperature), one can monitor the generation of PPi during the isothermal nucleic acid amplification reaction using a standard ELIDA reaction. An example of a mutant firefly luciferase enzyme that is stable at 37° C. and which is suitable for use in a method of the present invention is described by Tisi, L. et al. (Tisi, L. C. et al., (2002) 'Development of a thermostable firefly luciferase', Analytica Chimica Acta, Vol. 457, 115-123).

Alternatively, the nucleic acid amplification reaction of step ii) may be carried out at more than one temperature within the preferred temperature range.

Where it is found that the luciferase that is used produces a lower overall intensity of light output from the bioluminescence assay (whether amplification occurs or not) when the temperature at which the nucleic acid amplification reaction is performed is increased, it is advantageous for the nucleic acid amplification reaction of step ii) to be run at a lower temperature. This has the dual advantage that the intensity of light output is increased and that the amplification reaction occurs more slowly. A slower amplification reaction is particularly beneficial for quantitative analysis since the data points which correspond to the various points at which there is a variation in the rate of change of light intensity with time for samples having different amounts of the template nucleic acid occur over a greater period of time than when the amplification reaction is monitored at the higher temperature and are thus more easily monitored.

However, running the nucleic acid amplification reaction at a lower temperature could potentially affect the specificity of the amplification reaction. For example, there could be a greater chance of a false positive result as the temperature of the amplification reaction is reduced since the chance of primers annealing to sequences other than the desired target sequence increases as the temperature of the nucleic acid amplification reaction is reduced. Thus, the invention also provides a method in which the nucleic acid amplification reaction of step ii) is started at a higher temperature and subsequently dropped to a lower temperature. Preferably, this higher and lower temperature are within a preferred temperature range as discussed above. This has the advantage that the nucleic acid amplification reaction can be initiated at a higher temperature where specificity is greater, then, before amplification enters a detectable exponential phase, the temperature can be lowered to increase light intensity and slow the progress of the results.

The relatively low temperature of the isothermal methods and the low temperature thermocycling method compared to methods which utilise conventional thermocycling PCR in which the temperature is raised to 95° C. allows for smaller sample volumes to be analysed. In particular, in embodiments in which the temperature range does not exceed 55° C., exquisitely small sample volumes can be analysed by a method of the invention. For example, sample volumes of less than 10 µl and even sample volumes of less than 1 µl may be analysed by a method of the invention. The high temperatures required in conventional PCR make very small sample volumes a technical challenge. The ability to analyse very small sample volumes also has the advantage of cutting reagent costs.

Thus, in a preferred embodiment, a method of the invention requires that in the amplification reaction of step ii), the polymerase reaction is conducted isothermally and that the luciferase that is used is stable at that temperature. This offers the following advantages:

i) the isothermal nucleic acid amplification reaction could be monitored continuously in real-time;
ii) the isothermal nucleic acid amplification reaction could be monitored in a completely closed system without the need for further reagent addition;
iii) the relatively low temperature of the assay would allow exquisitely small sample volumes to be analysed (the high temperature of conventional PCR make very small samples volumes a technical challenge so cutting reagent costs; and
iv) a simple CCD camera could be employed to simultaneously monitor thousands of isothermal PCR reactions.

It is a feature of the invention that PPi from nucleic acid synthesis during nucleic acid amplification can be detected when the nucleic acid which has been synthesised would be undetectable by gel electrophoresis, resulting in increased sensitivity and reduced amplification time. Further, whilst the turbidity method of Mori et al (Mori, Y. et al., Biochem. Biophys. Res. Comm., (2001) 289, 150-154) requires PPi concentrations of ~0.6 mM before significant turbidity is observed, by using a pyrophosphate assay in which PPi is converted to ATP by ATP sulphurylase and by which the ATP produced is used by a luciferase to produce light, PPi concentrations of less than 0.5 µM result in a linear relationship between PPi concentration and bioluminescence (Nyren & Lundin, Analytical Biochemistry, 151(2), 405-409 (1985)). This represents an increase in sensitivity of a method of the invention for detecting PPi of at least 1200 times over a turbidity assay. The methods of the invention are also more sensitive than fluorescence-based methods.

A method according to the invention may be used in medical diagnostic applications. At present, most diagnostic test centres need to send off their tests for analysis since conventional methods for analysing nucleic acid amplification reactions such as PCR require complicated hardware and optics. The use of a method as described above will enable test results to be analysed at point-of-care. For example, it could be used in sexual health clinics, for instance to see whether a pathogen such as particular bacterium or virus is present in a sample. It may also be used to determine the amount of bacteria or virus present in a sample, for example, to determine the extent of an infection.

A further application of a method according to the invention is for determining whether a particular nucleic acid sequence is present in an organism's genetic code. For example, it could be used for determining whether the nucleic acid to which the template nucleic acid originates has been genetically modified, for detection of DNA associated with a particular non-genetically modified breed of plant or a genetically modified plant, for detection of DNA associated with pedigree breeds of animal or for medical or veterinary diagnostic applications such as genetic testing or forensics.

A method according to the invention may be used to detect the presence of an organism in a sample. As mentioned above, this organism may be a pathogen. However, the method may also be used to detect a non-pathogenic organism.

A method of the invention may also be used in immuno-nucleic acid amplification technology (for example, see Sano, T. et al., (1992) Science, vol. 258, 120-122) (e.g., for identification of a particular template nucleic acid linked to an antibody). The method is also suitable for use in situ where techniques such as fluorescence or absorbance would be technically difficult to use. For example, a method of the invention could be used on a metal surface. Thus a method of the invention could be used, for example, to look for prions on a scalpel blade.

A kit for use in a method according to the invention preferably comprises a nucleic acid polymerase, the substrates for the nucleic acid polymerase, at least two primers, a thermostable luciferase, luciferin and optionally ATP sulphurylase and adenosine 5' phosphosulphate. More preferably, the kit further comprises buffer reagents, such as a source of magnesium ions. Alternatively, a kit for use in a method according to the invention may comprise only some of these components and/or additional components. The sample and any other components that have been omitted from the kit may then be added to the kit during use.

For example, a kit for use in a method of the invention may comprise containers respectively containing:
a) a buffered mixture of nucleic acid polymerase, a source of Mg and dNTPs; and
b) a luciferase, luciferin and ATP sulphurylase.

Preferably, at least one of the components of the kit is lyophilised or is in another form which is suitable for storage in the kit. More preferably, all of the components of the kit are lyophilised or in one or more forms suitable for storage. Such other forms include components to which stabilising factors have been added and/or a refrigerated or frozen mastermix that contains the components of the kit.

A preferred form of kit is a miniature "liquid" circuit. Preferably, a kit for use in the present invention will be the size of a credit-card for ease of handling.

A kit for use in a method according to the invention can be used to analyse one sample at a time or more than one sample at a time. For example, a kit for use in a method according to the invention may be used to monitor 2, 3, . . . , 50, . . . , 100, . . . 200 up to 1000 s of samples at a time.

In embodiments in which a method of the present invention is used to monitor more than one sample at a time, the method may be for detecting the presence of a template nucleic acid of the same sequence in each sample or may be for detecting the presence of template nucleic acids having different sequences in different samples.

The results may be displayed on a test card that displays the results from one sample or more than one sample. Preferably, the test card is about the size of a credit card for ease of handling.

The invention further provides a device for performing a method of the invention and which incorporates the components that are present in a kit according to the invention. For example, a device according to the invention preferably incorporates a nucleic acid polymerase, the substrates for the nucleic acid polymerase, at least two primers, a thermostable luciferase, luciferin and optionally ATP sulphurylase and adenosine 5' phosphosulphate.

The invention will now be described further by way of example only with reference to the following figures in which:

FIG. 1 shows a set-up used to follow a LAMP reaction;
FIG. 2 shows the output from LAMP in the presence of target DNA and in a control without Bst DNA Polymerase;
FIG. 3 shows the results from duplicate LAMP samples and duplicate controls;
FIG. 4 shows the results from samples prepared as in FIGS. 2 & 3 but showing differences in absolute light intensity;
FIG. 5 shows the light emission profiles for LAMP using different amounts of target template (duplicates) at 55° C.;
FIG. 6 shows the time to peak light emission;
FIG. 7 shows a plot of the raw output from a LAMP reaction in triplicate;
FIG. 8 shows plots of the $1^{st}$ derivative of the curves shown in FIG. 7;
FIG. 9 shows a comparison of controls to samples;
FIG. 10 shows a LAMP reaction where the temperature is decreased from 55° C. to 50° C. after 10 minutes;
FIG. 11 shows a plot of the light intensity against time for ATP Sulphurylase-free LAMP with different amounts of starting template; and
FIG. 12 shows a differential plot (control subtracted) of the normalized light-outputs for the ATP Sulphurylase-free LAMP reactions of samples containing different amounts of target template.

EXAMPLES

Example 1

Demonstration of a Method of the Present Invention

The isothermal nucleic acid amplification reaction known as Loop-Mediated Amplification (LAMP) was selected to exemplify the potential for using a simple bioluminescent assay to follow nucleic acid amplification in real-time.

The present, most rapid manifestation of the LAMP method uses six primers. This manifestation has been demonstrated to detect $10^5$ copies of target DNA in just 15 minutes (Nagamine et al. 2002 Molecular and Cellular Probes, 16, p223-229). LAMP reactions normally run at 60-65° C. and require at least 4 mM of Magnesium ions.

In order to demonstrate a real-time bioluminescent output from a LAMP reaction in particular, it was necessary to find means to lower the temperature at which the LAMP reaction runs. This is due to the fact that at temperatures as high as 65° C. even the most thermostable beetle luciferase known to date (the Ultra-Glow thermostable luciferase from Promega) is not sufficiently active and/or stable to give sufficient and stable light output over the duration of a LAMP amplification (around 45 minutes or longer may be required to confirm that a sample does not contain any of a particular target DNA molecule).

It was recognized that lowering the concentrations of Magnesium ions from 4 mM to 2 mM allowed LAMP reactions to run successfully at lower temperatures. Further, high concentrations of Betaine can reduce the ability of LAMP reactions to reproducibly run successfully at lower temperatures. Finally, appropriate stabilizing agents that did not interfere with the LAMP reaction were selected and included in the formulations. As a result, it was possible to formulate conditions where a bioluminescence assay could occur simultaneously with a LAMP reaction over the full period of the amplification.

Starting Materials

1) Reaction Mixture (Less Bst-DNA Polymerase or Target DNA)

| Quantity | Reagent | Supplier |
|---|---|---|
| 20 mM | Tris-acetate | Sigma |
| 10 mM | KCl | " |
| 10 mM | Ammonium Sulphate | " |
| 2 mM | Magnesium Sulphate | " |
| 0.10% V/V | Triton X-100 | " |
| 0.5% W/V | BSA | " |
| 5% W/V | Trehalose | " |
| 0.4 mg/ml | Polyvinylpyrrolidone | " |
| 9 mM | Dithiothreitol | Melford |
| 100 μg/ml | D-luciferin (Potassium Salt) | Europa |
| 54 ng/ml | Ultra-Glow rLuciferase | Promega |
| 100 μM | Adenosine 5' phosphosulphate | Sigma |
| 0.5 U/ml | ATP Sulphurylase | " |
| 250 μM | Each of the four dNTPs | Amersham Biosci. |
| 0.8 μM | Lamp B1cB2 primer | PNAC Cambridge UK |
| 0.8 μM | Lamp F1F2c primer | " |
| 0.4 μM | Lamp Loop B primer | " |
| 0.4 μM | Lamp Loop F primer | " |
| 0.2 μM | Lamp B3 primer | " |
| 0.2 μM | Lamp F3c primer | " | pH 8.8 @ 25° C. (see below for primer sequences)

2) DNA polymerase
8 U/μl Bst DNA Polymerase New England Biolabs

3) Template DNA (SEQ ID NO:1)

catgaattctgtcaagtctacgataacttagcgcttaggatgtcagatac ttatgatgataagctgatagactatcttgcctggaagcttacttcataat ggatgacgtatgccatgatagataccattgtctagacataagactttcaa tctgcatagtcatgatcgatccatgctcgagtccaagctagtcatagctt atcatcaactgaatctagtaagtcattgaattctag Primer sequences (SEQ ID NOS:2-7):

```
Lamp B1cB2:    tat cat ggc ata cgt cat cca ttt
               tta taa gct gat aga cta tct tgc Lamp F1F2c:    tca atc tgc ata gtc atg atc gtt
               ttt tga tga taa gct atg act agc Lamp Loop B:   tat gaa gta agc ttc cag Lamp Loop F:   atc cat gct cga gtc caa Lamp B3 primer atg tca gat act tat gat g Lamp F3c primer aat gac tta cta gat tca g
```

Method

To a 200 μl PCR tube, 18.6 μl of the reaction mixture was added followed by 1 μl of 0.4 ng/μl Template DNA and 0.4 μl of Bst DNA polymerase. As a control in a further 200 μl PCR tube, 18.6 μl of the reaction mixture and 0.4 ng/μl of template DNA were added but no Bst DNA polymerase.

The samples were placed on a heating block held at 50° C. that had been placed inside a Syngene GeneGenius light cabinet (www.syngene.co.uk). Using the Syngene Genesnap software (www.syngene.co.uk), light emission from the samples was recorded (through the closed lids of the PCR tubes) in a series of pictures taken with a CCD camera within the Syngene light cabinet (FIG. 1). Each picture represented the integrated light emission from the sample over a period of 1 minute.

A total of 40 frames were recorded, hence the LAMP reaction was observed for 40 minutes in total.

Results

Using Syngene software, the light output from each of the samples was quantified as a function of time. The results obtained are shown in FIG. 2.

Using agarose gel electrophoresis it was confirmed that the 'sample' (with the template nucleic acid) had indeed amplified significant amounts of DNA while the control had synthesized none.

A number of features were noted about the light emission that resulted in the case of the amplification:

ii) Initially the rate of light decrease for the sample and the control were similar;

ii) After a period, the light intensity from the sample started to increase, whilst the control continued to decrease gradually;

iii) The rate of increase in light emission from the sample increased, reached a maximum, then decreased until a point was reached where the greatest magnitude of light emission during the LAMP reaction was recorded;

iv) Following this maximum in light emission from the sample, a decrease in light emission was observed;

v) The rate of decrease in light emission increased following the maximal light emission and the magnitude of the light emission became less than that of the control;

vi) The rate of decrease in light emission decreased and eventually became similar to that of the control;

vii) At the end of the 40 minutes, the magnitude of light emission from the sample was considerably less than the control even though, in this case, the starting light intensity of the sample was slightly higher (which is related to the fact that the light emission from the samples was not processed in any way to take account of the relative position of the samples relative to the camera).

It is hypothesised that the decrease in light intensity following the peak in light intensity is as a result of luciferase becoming inhibited by pyrophosphate. As such, in the LAMP reaction, the peak in light intensity represents a point in time when a specific amount of pyrophosphate has accumulated. Therefore, the peak in light intensity represents a point in time when a specific amount of DNA has been synthesized.

Example 2

Reproducibility of the Method of the Invention Using a Lamp Amplification Reaction The same procedure was carried out as in example 1 except that multiple samples were used to assess the reproducibility of results obtained in the LAMP reaction.

Starting Materials and Methods

As for example 1 except the sample and control were performed in duplicate or triplicate and the temperature of the reaction was raised to 55° C.

Results

The results are shown in FIG. 3. The same progress of the sample curve as in Example 1 is seen in this case.

In this example both the rate of change of light emission and the time to maximal light emission are extremely similar for both of the samples. Again, generation of amplified DNA in the samples was confirmed by agarose gel electrophoresis. For the controls, whilst the rate of change of light emission for both cases are similar, there is a small difference in absolute value. Again, this is thought to be because of the effects associated with light capture by the system used rather than any biochemical aspect. Nonetheless, even without data manipulation, clear-cut results can be obtained.

In some cases, the absolute light intensity observed within e.g. triplicate samples could vary due to light capture effects. Nonetheless the rate of light change and the time to maximal light emission is similar (FIG. 4).

Example 3

Use of a Method of the Invention in a Quantitative Fashion

Starting Materials and Methods

The same procedure outlined in example 1 was repeated but with different amounts of target DNA in the samples. Duplicate samples were set up containing a total of either 0.4 ng, 40 pg, 4 pg or 0.4 pg of template nucleic acid. The temperature of the LAMP reaction was 55° C.

Results

The resulting light emission profiles for each of the samples is shown in FIG. 5. The results obtained in FIG. 5 demonstrate a key property of methods of the invention. Whilst there is not a convincing correlation between the amount of target template and absolute light emission, there is a clear relationship between the time to peak light emission or the time to changes in the rate of change of light emission.

A plot of time to peak light emission against amount of target DNA demonstrates that the correlation is quantitative (see FIG. 6a in which the time to peak light emission has a linear correlation with the log 10 of the concentration of DNA target Template in the sample). In FIG. 6b, the time to produce 25% of the final total amount of amplicon is plotted with the time to peak light emission and it can be seen that the two parameters correlate. Thus, comparing the times to peak light emission against results obtained with agarose gel electrophoresis demonstrates that the time to peak light emission reflects the accumulation of amplicon and thus the amount of template nucleic acid present in the sample Example 4

Data Manipulation of Results from a Method of the Invention in which the Nucleic Acid Amplification Reaction is a LAMP Reaction The same procedure as in example 1 was carried out again but using multiple samples to assess the reproducibility of results obtained in the LAMP reaction after some simple data manipulation of the raw data had been performed. Specifically, the $1^{st}$ derivative of the outputs were plotted.

Starting Materials and Methods

These were as for Example 1 except that the sample and control were performed in triplicate, the temperature was 50° C. and a total of 1 ng of template was used in each sample.

FIG. 7 shows a plot of the raw data from a method of the invention on these samples. By plotting the rate of change in light emission over time as opposed to the light intensity over time (i.e. plotting the $1^{st}$ derivative), inflection points are highlighted. In particular, regions of the curves shown in FIG. 7 that go through minima or maxima intersect the Y axis at zero when the $1^{st}$ derivative of the curve is plotted (FIG. 7). While the magnitude of the intensities shows considerable variance, inflection points within sets of the curves are similar.

The curves in FIG. 8 for the samples where a LAMP amplification reaction has occurred show two points crossing the Y-axis. The first represents the first inflection point of FIG. 7 and the second represents the point of maximum light intensity. The minima and maxima seen in FIG. 8 highlight time-points associated with maximal rates of change in light emission. All four data points (the two Y-axis intersections and the minima and maxima) show good superposition between the triplicate samples. Note that the first Y-axis intersection occurs almost ten minutes before the second.

FIG. 9 shows an expanded view of the curves of FIG. 8 and highlights how plotting the $1^{st}$ derivative differentiates the sample from the control.

Thus due to the inherent information content of the raw data from a method of the invention using a LAMP reaction, even very simple data manipulation, such as taking the $1^{st}$ derivative, not only allows clear points on the resulting curves to be identified (Y-axis intersections and maxima and minima) but also makes the results less sensitive to the magnitude of the light signals (e.g. compare the superposition of the curves in FIGS. 7 and 8—in FIG. 8 the superposition is more similar).

Example 5

Changing Temperature of the Amplification Reaction During Amplification

The LAMP method can be made to work over the temperature range of approximately 45° C. to 65° C. However, the higher the temperature at which the LAMP reaction is run, the lower the overall light intensity from a method of the invention (whether amplification occurs or not). This is due to the particular thermostable luciferase used (the Ultra-Glow luciferase from Promega) apparently catalysing the light reaction at a lower rate at higher temperatures. Thus the rate of light emission observed for the Ultra-Glow luciferase at 55° C. is considerably less than that observed at 50° C. However, on cooling from e.g. 55° C. to 50° C., one observes an increase in the rate of light emission catalyzed by the Ultra-Glow luciferase, hence the effect is clearly reversible. The reversibility implies that the observed decrease in light emission at high temperature is not solely the result of the luciferase denaturing.

Running a LAMP reaction at a lower temperature hence increases the light emission from the assay. Further, running LAMP at lower temperatures can slow the reaction itself. This may be beneficial in certain circumstances. For example, when using a method of the invention quantitatively, there may be benefits in slowing the amplification so that the times taken to, e.g. reach peak light emission for samples with different amounts of target template, are more greatly separated in time than when the LAMP reaction is run at a higher temperature.

However, running LAMP reactions at low temperatures could potentially affect the specificity of the process, that is, there could be a greater chance of a false-positive result as the temperature of the LAMP is reduced. In other words, the chances of primers annealing to sequences other than the desired target sequence, increases as the temperature of the LAMP reaction is reduced.

A possible compromise to take advantage of benefits of running the LAMP reaction at low temperatures and yet maintaining the maximal specificity is to change temperature during the LAMP reaction. Specifically, the LAMP reaction can be initiated at a higher temperature where specificity is greater, then, before amplification enters a detectable exponential phase, the temperature can be lowered to increase light intensity and slow the progress of results.

Starting Materials and Methods

As for Example 1 except that a variety of samples were tested with different amounts of target template as in Example 3 (over the range 0.02 pg/µl to 20 pg/µl, i.e., 0.4 pg total sample to 0.4 ng total sample). The LAMP reaction was initiated at 55° C. then the temperature lowered to 50° C. after 10 minutes.

Results

The raw data obtained from the temperature change data is shown in FIG. 10. The data shown in FIG. 10 show that the temperature change method does indeed result in an increase in the intensity of light emission on dropping the temperature. Further, the LAMP remains quantitative, in that the time to peak light emission remains a function of the starting amount of template DNA. Comparing FIG. 10 to FIG. 5, where equivalent amounts of target template are tested with LAMP but at a single temperature of 55° C., it can be seen that the time difference between the sample with the most template (0.4 ng total/20 pg/ul) and least template (0.4 pg total/0.02 pg/ul) is approximately 8 minutes, whereas in the temperature change method shown in FIG. 10, the time difference is approximately 14 minutes.

In fact, temperatures higher than 55° C. may initially be used, since, though the Ultra-Glow luciferase begins to become unstable above 60° C., it can tolerate being at higher temperatures for short periods. This approach therefore increases the temperature ranges available.

Further, this approach may enable less stable luciferases to be employed where the amplification reaction does not require long periods at temperatures that can irreversibly inactivate luciferase.

Finally, whilst clearly false-positives can still occur using the temperature change method, they should be less common due to the increased stringency of the higher temperatures at the initial key phase of amplification (i.e. just prior to exponential phase).

Example 6

Reversibly-Inhibited Luciferase-Based Method

As discussed above, pyrophosphate has direct effects on luciferase. Firstly, under certain circumstances, pyrophosphate can relieve the inhibition luciferase undergoes in the presence of certain inhibitors including oxyluciferin, the product of the light reaction. Secondly, pyrophosphate can itself inhibit luciferase at high concentrations. Whether or not pyrophosphate stimulates or inhibits the light emitting reaction catalyzed by luciferase depends on a number of factors including the precise type of luciferase, temperature, concentration of pyrophosphate, presence of other compounds that can affect luciferase activity. This example shows how the inhibitory effect of pyrophosphate can be used to follow a LAMP reaction. A vital aspect of this approach is that the presence of ATP in the sample can be tolerated: in methods in which the bioluminescence assay relies on the detection of ATP by the luciferase for the production of light, significant amounts of endogenous ATP in the sample would severely compromise the use of the assay.

The fact that the ATP Sulphurylase-free method tolerates ATP (in fact it works best in the presence of ATP) means that it can potentially be used to assay for pyrophosphate in amplification reactions that include an RNA synthesis step such as Transcription Mediated Amplification (TMA).

By carrying out control experiments under a particular set of reaction conditions, the skilled person will be able to determine the particular ratio of luciferase to luciferin to ATP to pyrophosphate (luciferase:luciferin:ATP:PPi) that is required for use in a method of the invention.

Starting Materials and Methods

1) ATP Sulphurylase-Free Reaction Mixture (Less Bst-DNA Polymerase or Target DNA)

| Quantity | Reagent | Supplier |
|---|---|---|
| 20 mM | Tris-acetate | Sigma |
| 10 mM | KCl | " |
| 10 mM | Ammonium Sulphate | " |
| 2 mM | Magnesium Sulphate | " |
| 0.10% V/V | Triton X-100 | " |
| 0.5% W/V | BSA | " |
| 5% W/V | Trehalose | " |
| 0.4 mg/ml | Polyvinylpyrrolidone | " |
| 9 mM | Dithiothreitol | Melford |
| 1 µg/ml | D-luciferin (Potassium Salt) | Europa |
| 36 ng/ml | Ultra-Glow rLuciferase | Promega |
| 1 mM | Adenosine triphosphate (ATP) | Sigma |
| 250 µM | Each of the four dNTPs | Amersham Biosci. |
| 0.8 µM | Lamp B1cB2 primer | PNAC Cambridge UK |
| 0.8 µM | Lamp F1F2c primer | " |
| 0.4 µM | Lamp Loop B primer | " |
| 0.4 µM | Lamp Loop F primer | " |
| 0.2 µM | Lamp B3 primer | " |
| 0.2 µM | Lamp F3c primer | " | pH 8.8 @ 25° C. (see below for primer sequences)

Method

Samples were prepared as in Example 1 except using the reaction mixture described above. A range of target template DNA concentrations were tested, from 1 pg to 1 ng. The ATP sulphurylase-free LAMP was run at 55° C. A Bst DNA polymerase-free sample was used as the control.

Results

The raw data resulting from the ATP sulphurylase-free LAMP are shown in FIG. 11. The raw data shown in FIG. 11 shows that the samples containing template nucleic acid show a characteristic sudden decrease in light intensity over time, not seen in the control. This decrease is believed to be the result of pyrophosphate produced by the LAMP reaction inhibiting the luciferase. As such the sudden decrease is a marker for nucleic acid amplification. That DNA synthesis was actually occurring was confirmed by agarose gel electrophoresis of the samples.

Data manipulation of the raw data enabled further interpretation of the results. Firstly, the data were normalized to their starting light intensities, then the values obtained from the control lacking polymerase were subtracted from that of the template nucleic acid-containing samples (FIG. 12).

Examination of FIG. 12 indicates that the ATP sulphurylase-free LAMP is also quantitative, as the time taken to reach points where the rate of change of light intensity significantly changes, appears to be proportional to the concentration of target template in the samples.

Since 1 mM ATP is present during the ATP sulphurylase-free LAMP, the same approach can therefore be taken to follow RNA-based amplification methods.

It will be appreciated that the invention has been described above by way of example only and that further modifications in detail may be made which remain within the scope of the invention as defined by the claims.

The invention claimed is:

1. A method for determining the amount of template nucleic acid present in a sample comprising:
   i) bringing into association with the sample all the components necessary for nucleic acid amplification, and all the components necessary for a bioluminescence assay for nucleic acid amplification including:
      a) a nucleic acid polymerase,
      b) the substrates for the nucleic acid polymerase,
      c) at least two primers,
      d) a thermostable luciferase,
      e) luciferin,
      f) ATP sulphurylase, and
      g) adenosine 5' phosphosulphate;
   and subsequently:
   ii) performing a nucleic acid amplification reaction of the template nucleic acid involving more than one cycle of amplification;
   iii) monitoring the intensity of light output from the bioluminescence assay; and
   iv) determining the amount of template nucleic acid present in the sample.

2. A method according to claim 1, wherein at least ii) and iii) are carried out in a sealed vessel.

3. A method according to claim 1, wherein in iii) the intensity of light output is monitored during the nucleic acid amplification reaction.

4. A method according to claim 1, wherein iii) further includes producing a data set of intensity of light output as a function of time.

5. A method according to claim 4, wherein the amount of template nucleic acid present is determined by measuring from the data set the time taken to reach a point at which the rate of change of intensity of light output changes significantly.

6. A method according to claim 1, wherein the amount of template nucleic acid present in the sample before the nucleic acid amplification reaction of ii) is determined.

7. A method according to claim 1, wherein the amount of template nucleic acid present in the sample after the nucleic acid amplification reaction of ii) is determined.

8. A method according to claim 5, wherein the amount of template nucleic acid present is determined by measuring from the data set the time taken to reach a point at which the intensity of light output begins to increase.

9. A method according to claim 5, wherein the amount of template nucleic acid present is determined by measuring from the data set the time taken to reach a point at which the intensity of light output is at a maximum.

10. A method according to claim 5, wherein the amount of template nucleic acid present is determined by measuring from the data set the time taken to reach a point at which the rate of decrease of intensity of light output increases.

11. A method according to claim 5, wherein the amount of template nucleic acid present is determined by measuring from the data set the time taken to reach a point at which the rate of decrease of intensity of light output decreases.

12. A method according to claim 5, wherein the amount of template nucleic acid present is determined by measuring from the data set the time taken to reach a point at which the intensity of light output reaches or crosses a predetermined level.

13. A method according to claim 8, wherein the thermostable luciferase that is brought into association with the sample in i) is a reversibly-inhibited luciferase.

14. A method according to claim 1, wherein iv) further comprises comparing the intensity of light output to the intensity of light output from a control in which the sample comprises a known amount of template nucleic acid.

15. A method according to claim 1 for determining whether the template nucleic acid is present in the sample, wherein whether the template nucleic acid is present in the sample is determined by measuring from the data set whether the intensity of light output reaches or crosses a predetermined level.

16. A method according to claim 15, wherein an increase in the intensity of light output relative to the predetermined level indicates the presence of template nucleic acid in the sample.

17. A method according to claim 15, wherein a decrease in the intensity of light output relative to the predetermined level indicates the presence of template nucleic acid in the sample.

18. A method according to claim 15, wherein whether the template nucleic acid is present in the sample is determined by measuring from the data set whether the intensity of light output reaches or crosses the predetermined level within a predetermined length of time following the start of the amplification reaction of ii).

19. A method according to claim 1, wherein iv) further comprises comparing the intensity of light output to the intensity of light output from a control in which no amplification has taken place.

20. A method according to claim 19, wherein a decrease in the intensity of light output relative to a control reaction in which no amplification has taken place indicates the presence of template nucleic acid in the sample.

21. A method according to claim 1, wherein the nucleic acid amplification reaction of ii) is a low temperature thermocycling amplification method in which the cycling temperature range does not exceed 75° C.

22. A method according to claim 1, wherein the nucleic acid amplification reaction of ii) is carried out isothermally.

23. A method according to claim 22, wherein the nucleic acid amplification reaction of ii) is carried out within a temperature range that does not exceed 75° C.

24. A method according to claim 22, wherein the nucleic acid amplification reaction of ii) is carried out at a constant temperature at which the components of the amplification reaction and the bioluminescence assay are stable.

25. A method according to claim 22, wherein the nucleic acid amplification reaction of ii) is carried out at more than one temperature within the temperature range in which the components of the amplification reaction and the bioluminescence assay are stable.

26. A method according to claim 25, wherein the nucleic acid amplification reaction of ii) is started at a higher temperature and subsequently dropped to a lower temperature.

27. A method according to claim 1 further comprising determining a medical diagnosis.

28. A method according to claim 1 further comprising determining whether a pathogen is present in a sample.

29. A method according to claim 1 further comprising determining whether a particular nucleic acid sequence is present in an organism's genetic code.

30. A method according to claim 29 further comprising determining whether the nucleic acid to which the template nucleic acid originates has been genetically modified.

31. A method according to claim 1 further comprising determining whether an organism is present in a sample.

32. A method according to claim 1, wherein the template nucleic acid is linked to an antibody.

33. A method for determining the amount of template nucleic acid present in a sample comprising:
  i) bringing into association with the sample all the components necessary for nucleic acid amplification, and all the components necessary for a bioluminescence assay for nucleic acid amplification including:
    a) a nucleic acid polymerase,
    b) the substrates for the nucleic acid polymerase,
    c) at least two primers,
    d) a thermostable luciferase, and
    e) luciferin;
and subsequently:
  ii) performing a nucleic acid amplification reaction of the template nucleic acid involving more than one cycle of amplification;
  iii) monitoring the intensity of light output from the bioluminescence assay; and
  iv) determining the amount of template nucleic acid present in the sample.

* * * * *

```
                          SEQUENCE LISTING

<160> NUMBER OF SEQ ID NOS: 7

<210> SEQ ID NO 1
<211> LENGTH: 235
<212> TYPE: DNA
<213> ORGANISM: Artificial Sequence
<220> FEATURE:
<223> OTHER INFORMATION: template DNA

<400> SEQUENCE: 1
catgaattcg tcaagtctac gataacttag cgcttaggat gtcagatact tatgatgata      60
agctgataga ctatcttgcc tggaagctta cttcataatg gatgacgtat gccatgatag     120
ataccattgt ctagacataa gactttcaat ctgcatagtc atgatcgatc catgctcgag     180
tccaagctag tcatagctta tcatcaactg aatctagtaa gtcattgaat tctag          235

<210> SEQ ID NO 2
<211> LENGTH: 48
<212> TYPE: DNA
<213> ORGANISM: Artificial Sequence
<220> FEATURE:
<223> OTHER INFORMATION: primer

<400> SEQUENCE: 2
tatcatggca tacgtcatcc atttttataa gctgatagac tatcttgc                   48

<210> SEQ ID NO 3
<211> LENGTH: 48
<212> TYPE: DNA
<213> ORGANISM: Artificial Sequence
<220> FEATURE:
<223> OTHER INFORMATION: primer

<400> SEQUENCE: 3
tcaatctgca tagtcatgat cgttttttga tgataagcta tgactagc                   48

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
tatgaagtaa gcttccag                                                    18

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
atccatgctc gagtccaa                                                    18
```

```
<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
atgtcagata cttatgatg                                            19

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
aatgacttac tagattcag                                            19
```